US010232035B2

(12) United States Patent
Mahalingam et al.

(10) Patent No.: US 10,232,035 B2
(45) Date of Patent: Mar. 19, 2019

(54) CONDITIONALLY REPLICATION DEFICIENT HERPES VIRUS AND USE THEREOF IN VACCINES

(71) Applicant: THE REGENTS OF THE UNIVERSITY OF COLORADO, A BODY CORPORATE, Denver, CO (US)

(72) Inventors: Ravi Mahalingam, Aurora, CO (US); Donald Gilden, Greenwood Village, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/427,918

(22) PCT Filed: Sep. 11, 2013

(86) PCT No.: PCT/US2013/059192
§ 371 (c)(1),
(2) Date: Mar. 12, 2015

(87) PCT Pub. No.: WO2014/043189
PCT Pub. Date: Mar. 20, 2014

(65) Prior Publication Data
US 2016/0008458 A1 Jan. 14, 2016

Related U.S. Application Data

(60) Provisional application No. 61/701,226, filed on Sep. 14, 2012.

(51) Int. Cl.
*A61K 39/245* (2006.01)
*A61K 39/25* (2006.01)
*C12N 7/00* (2006.01)
*A61K 39/12* (2006.01)
*A61K 39/00* (2006.01)

(52) U.S. Cl.
CPC .............. *A61K 39/25* (2013.01); *A61K 39/12* (2013.01); *A61K 39/245* (2013.01); *C12N 7/00* (2013.01); *A61K 2039/5254* (2013.01); *A61K 2039/544* (2013.01); *A61K 2039/70* (2013.01); *C07K 2319/00* (2013.01); *C12N 2710/16034* (2013.01); *C12N 2710/16634* (2013.01); *C12N 2710/16722* (2013.01); *C12N 2710/16734* (2013.01); *C12N 2710/16762* (2013.01)

(58) Field of Classification Search
None
See application file for complete search history.

(56) References Cited

U.S. PATENT DOCUMENTS

| 3,985,615 A | 10/1976 | Kubo |
| 4,912,094 A | 3/1990 | Myers et al. |
| 5,057,540 A | 10/1991 | Kensil et al. |
| 2008/0279886 A1 | 11/2008 | Cohen et al. |

FOREIGN PATENT DOCUMENTS

| EP | 0 109 942 | 5/1984 |
| EP | 0 192 902 | 9/1986 |
| EP | 0 362 279 | 4/1990 |
| EP | 0 405 867 | 1/1991 |
| EP | 0 468 520 | 1/1992 |
| EP | 0 549 074 | 6/1993 |
| EP | 1 721 981 | 11/2006 |
| GB | 2 122 204 | 1/1984 |
| GB | 2 220 211 | 1/1990 |
| WO | WO 1994/00153 | 1/1994 |
| WO | WO 1994/02596 | 2/1994 |

(Continued)

OTHER PUBLICATIONS

Perng et al., Journal of Virology, May 2011, 85(10):4841-4852).*
Cohen et al., Journal of Virology, Nov. 2004, 78(21):11833-11840.*
CDC MMWR Weekly, Dec. 2, 2005, 54(47):1212-1214, website printout 4 pages, available from http://www.cdc.gov/mmwr/preview/mmwrhtml/mm5447a4.htm.*
Arvin AM, et al. "Live attenuated varicella vaccine," Annu Rev Microbiol. 1996;50:59-100.
Brazeau E, et al. "Simian varicella virus open reading frame 63/70 expression is required for efficient virus replication in culture," J Neurovirol. Jun. 2011;17(3):274-80.

(Continued)

*Primary Examiner* — Stacy B Chen
(74) *Attorney, Agent, or Firm* — Saul Ewing Arnstein & Lehr LLP; Kathryn Doyle; Domingos J. Silva

(57) ABSTRACT

The present invention is directed to a mutated recombinant herpesvirus, e.g., varicella zoster virus (VZV) and simian varicella virus strains or HSV-1 or HSV-2 strains, vaccines containing, and methods for the construction and use thereof to elicit protective immunity in susceptible individuals, wherein the particular herpesvirus is modified to render the virus replication deficient, i.e., the virus substantially or only replicates under defined conditions, by the incorporation of at least one destabilization domain in or fused to a gene essential for herpesvirus replication. The invention particularly relates to the use of the resultant conditionally replication defective herpesviruses, e.g., a mutated VZV strains in vaccine compositions in order to immunize individuals against herpesvirus infection, e.g., in the case of VZV chickenpox and to protect against shingles and zoster, or to prevent the reactivation of VZV or other herpesvirus reactivation and the onset of shingles or another condition relating to the reactivation of another herpesvirus infection, e.g., as a consequence of advanced age, stress, inflammation, drug or other therapy, cancer, or immunodeficiency such as in HIV-AIDS or other diseases resulting in impaired T and/or B cell immunity.

16 Claims, 17 Drawing Sheets

Specification includes a Sequence Listing.

(56) References Cited

FOREIGN PATENT DOCUMENTS

| WO | WO 1995/17210 | 6/1995 |
|---|---|---|
| WO | WO 1996/02555 | 2/1996 |
| WO | WO 1996/11711 | 4/1996 |
| WO | WO 1996/33739 | 10/1996 |
| WO | WO 1998/43670 | 10/1998 |

OTHER PUBLICATIONS

Breuer J. "Vaccination to prevent varicella and shingles," J Clin Pathol. Oct. 2001;54(10):743-7.
Chen JJ, et al. "Latent and lytic infection of isolated guinea pig enteric ganglia by varicella zoster virus," J Med Virol. 2003;70 Suppl 1:S71-8.
de Silva S, et al. "Herpes Virus Amplicon Vectors," Viruses. Dec. 1, 2009;1(3):594-629.
Debrus S, et al. "Varicella-zoster virus gene 63 encodes an immediate-early protein that is abundantly expressed during latency," J Virol. May 1995;69(5):3240-5.
Dendouga N, et al. "Cell-mediated immune responses to a varicella-zoster virus glycoprotein E vaccine using both a TLR agonist and QS21 in mice," Vaccine. Apr. 26, 2012;30(20):3126-35.
Goldman GS, et al. "Review of the United States universal varicella vaccination program: Herpes zoster incidence rates, cost-effectiveness, and vaccine efficacy based primarily on the Antelope Valley Varicella Active Surveillance Project data," Vaccine. Mar. 25, 2013;31(13):1680-94.
Iwamoto M, et al. "A general chemical method to regulate protein stability in the mammalian central nervous system," Chem Biol. Sep. 24, 2010;17(9):981-8.
Kennedy PG, et al. "Varicella-Zoster virus gene expression in latently infected rat dorsal root ganglia," Virology. Oct. 25, 2001;289(2):218-23.
Krause PR, et al. "Varicella vaccination: evidence for frequent reactivation of the vaccine strain in healthy children," Nat Med. Apr. 2000;6(4):451-4.
Lowry PW, et al. "Investigation of the pathogenesis of varicella-zoster virus infection in guinea pigs by using polymerase chain reaction," J Infect Dis. Jan. 1993;167(1):78-83.
Mahalingam R, et al. "Latent varicella-zoster viral DNA in human trigeminal and thoracic ganglia," N Engl J Med. Sep. 6, 1990;323(10):627-31.
Ouwendijk WJ, et al. "T-Cell tropism of simian varicella virus during primary infection," PLoS Pathog. May 2013;9(5):e1003368.
Oxman MN, et al. "A vaccine to prevent herpes zoster and postherpetic neuralgia in older adults," N Engl J Med. Jun. 2, 2005;352(22):2271-84.
Perng YC, et al. "The human cytomegalovirus gene UL79 is required for the accumulation of late viral transcripts," J Virol. May 2011;85(10):4841-52.
Quan D, et al. "Prevention of shingles: safety and efficacy of live zoster vaccine," Ther Clin Risk Manag. Aug. 2007;3(4):633-9.
Sadzot-Delvaux C, et al. "An in vivo model of varicella-zoster virus latent infection of dorsal root ganglia," J Neurosci Res. May 1990;26(1):83-9.
Tenser RB, et al. "Latent herpesvirus infections of neurons in guinea pigs and humans," Yale J Biol Med. Mar.-Apr. 1987;60(2):159-67.
Tischer BK, et al. Two-step red-mediated recombination for versatile high-efficiency markerless DNA manipulation in *Escherichia coli*, Biotechniques. Feb. 2006;40(2):191-7.
Vafai A. "Boosting immune response with a candidate varicella-zoster virus glycoprotein subunit vaccine," Vaccine. Oct. 1995;13(14):1336-8.
White TM, et al. "Simian varicella virus DNA is present and transcribed months after experimental infection of adult African green monkeys," J Neurovirol. Jun. 2002;8(3):191-203.
Wroblewska Z, et al. "A mouse model for varicella-zoster virus latency," Microb Pathog. Aug. 1993;15(2):141-51.

* cited by examiner

Figure 6

SVV mutant 2 with decreasing concentrations of TMP

| 10 μM | 5 μM | $1 \times 10^{-1}$ μM |
| $5 \times 10^{-2}$ μM | $5 \times 10^{-3}$ μM | $1 \times 10^{-3}$ μM |

Figure 7

| before TMP removal | after TMP removal | TMP added back |

FIGURE 11

Infection of Indian RM with SVV mutant 2 and SVVEGFP. Four Indian rhesus macaques were used for the experimental inoculation (Fig 11). They were divided into two groups. One monkey for each group was treated with 3.3 mg/kg of TMP for 3 days. The second one each group was untreated. The monkeys were then inoculated intrabronchially with $6 \times 10^4$ pfu of either SVV mutant 2 (group 1) or SVVEGFP (group 2). No varicella rash was seen in any of the monkeys. The monkeys were euthanized on 14 dpi and ganglia were collected for analysis.

Fig. 12 removed EGFP

Wild type SVV

TRL —— UL —— IRL/IRS | US | TRS
ORF 63
ORF 70 mutant ud63

TRL —— UL —— IRL/IRS | US | TRS
RFP
ORF 70-DHFR

Fig. 13

Effect of TMP reduction on mutant SVV replication 10 nM 100 nM 1000 nM

Fig. 14

Effect of TMP reduction and add back on SVV replication before TMP removal after TMP removal TMP added back

Fig. 17 intrabronchial
inoculation
with mutant SVV euthanized and analyzed
tissues for SVV DNA by PCR monkey 1 ──────────────→ −TMP monkey 2 ──────────────→ +TMP   no rash
                                 no viremia dpi −3      0                      +15 treat with TMP

Fig. 18
Preparation of new mutant dd63 SVV (with DHFR at the C-terminal end of ORF63/70)

Fig. 19

Effect of TMP reduction and add back on replication of new SVV mutant (dd63)

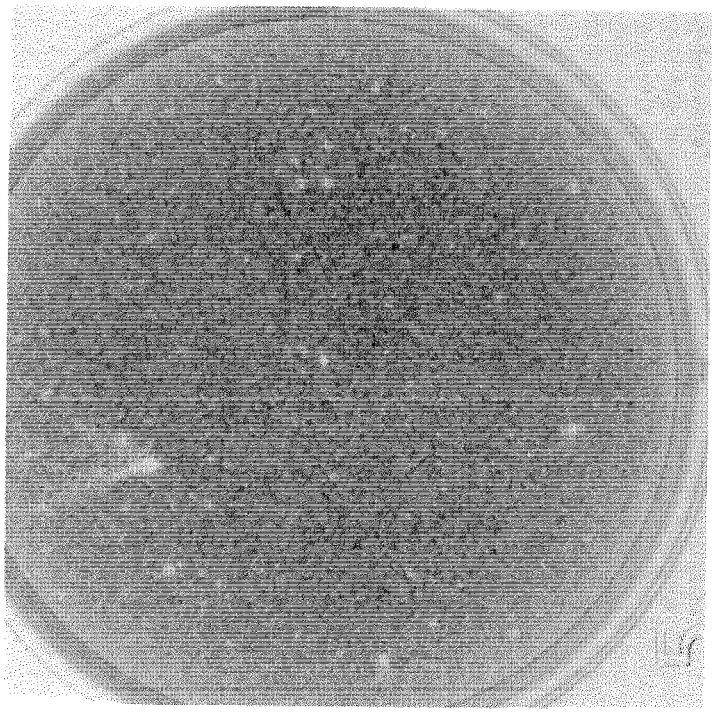
Fig. 22 Reduced number of mutant HSV-1 plaques without TMP

SEQUENCE LISTING

```
<160> NUMBER OF SEQ ID NOS: 2

<210> SEQ ID NO 1
<211> LENGTH: 477
<212> TYPE: DNA
<213> ORGANISM: Escherichia coli

<400> SEQUENCE: 1
atgatcagtc tgattgcggc gttagcggta gattacgtta tcggcatgga aaacgccatg      60
ccgtggaacc tgcctgccga tctcgcctgg tttaaacgca acaccttaaa taaacccgtg     120
attatgggcc gccatacctg ggaatcaatc ggtcgtccgt tgccaggacg caaaaatatt     180
atcctcagca gtcaaccgag tacggacgat cgcgtaacgt gggtgaagtc ggtggatgaa     240
gccatcgcgg cgtgtggtga cgtaccagaa atcatggtga ttggcggcgg tcgcgttatt     300
gaacagttct tgccaaaagc gcaaaaactg tatctgacgc atatcgacgc agaagtggaa     360
ggcgacaccc atttcccgga ttacgagccg gatgactggg aatcggtatt cagcgaattc     420
cacgatgctg atgcgcagaa ctctcacagc tattgctttg agattctgga gcggcga       477

<210> SEQ ID NO 2
<211> LENGTH: 159
<212> TYPE: PRT
<213> ORGANISM: Escherichia coli

<400> SEQUENCE: 2

Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

CONDITIONALLY REPLICATION DEFICIENT HERPES VIRUS AND USE THEREOF IN VACCINES

CROSS-REFERENCE TO RELATED APPLICATIONS

The present application is a 35 U.S.C. § 371 national phase application of, and claims priority to, International Application No. PCT/US2013/059192, filed Sep. 11, 2013, which claims priority under 35 U.S.C § 119(e) to U.S. provisional patent application Ser. No. 61/701,226, filed Sep. 14, 2012, all of which applications are incorporated herein by reference in their entireties.

STATEMENT REGARDING FEDERALLY SPONSORED RESEARCH OR DEVELOPMENT

This invention was made with government support under grant number AG032958 awarded by the National Institutes of Health. The government has certain rights in the invention.

SEQUENCE LISTING

The sequence listing file named "43898o1000.txt" having a size of 2,506 bytes and created Sep. 23, 2015, is hereby incorporated by reference in its entirety.

BACKGROUND

Field

The present disclosure is directed to the creation of variant or mutagenized herpes viruses and host cells containing, including but not limited to SVV, HSV-1, HSV-2, VZV, CMV, EBV, HHV6, HH7 and KSHV/HHV8, which variants or mutagenized viruses are rendered conditionally replication defective by the incorporation or fusion of one or more destabilization domains onto one or more genes which are essential for viral replication. In an exemplary embodiment the present invention is directed to a recombinant varicella virus (VV) strain and methods for the construction thereof, wherein the virus absent modification is prone to becoming latent or dormant in the ganglia and reactivating to cause zoster or shingles, and wherein the varicella virus, preferably varicella zoster virus (VZV) or simian varicella virus (SVV), is modified to render the virus conditionally replication deficient, i.e., the virus only replicates under defined conditions.

In an exemplary embodiment the present invention is directed to a recombinant herpes simplex virus 1 or 2 strain and methods for the construction thereof, wherein the virus is similarly modified to render the virus conditionally replication deficient, i.e., the virus only replicates under defined conditions, such as by the incorporation or fusion of one or more destabilization domains onto one or more genes essential for virus replication, e.g., the DNA polymerase gene.

The invention further specifically relates to the use of the resultant conditional replication defective VZV strains in vaccine compositions in order to immunize individuals against shingles and zoster, especially in order to prevent shingles in individuals who would otherwise be susceptible to reactivation of VZV and the onset of shingles e.g., based on advanced age, cancer, or immunodeficiency such as HIV-AIDS or another disorder resulting in impaired T cell function.

In another exemplary embodiment the present invention is directed to recombinant herpes simplex 1 or 2 (HSV-1, HSV-2) virus strains, cells and vaccines containing, and methods for the construction thereof, wherein the virus is rendered conditionally replication defective by the incorporation or fusion of a destabilization domain onto one or several genes essential for HSV-2 replication, e.g., the DNA polymerase and/or ICP4 genes. In a related aspect it is an object to provide vaccine compositions containing and the use thereof in order to immunize individuals against these herpes viruses.

Description of Related Art

Varicella Zoster Virus: Varicella zoster virus (VZV) causes chickenpox (varicella) in children. After varicella, VZV becomes latent in ganglia along the entire neuraxis (Mahalingam et al., 1990) and spontaneously reactivates decades later resulting in zoster (shingles), characterized by pain and rash restricted to 1-3 dermatomes. Each year, 600,000 to 1 million Americans are affected by zoster (NIH Shingles Prevention Study: www.niaid.nih.gov).

In the aging population, although VZV-specific humoral immunity is intact (Gershon and Steinberg, Am. J. Med. Sci. 1981 July-August;282(1):12-7), a decline in cell-mediated immunity to VZV (Miller, Neurology. 1980 June;30(6):582-7) correlates with the incidence of zoster (Arvin A M. Varicella-zoster virus. In: Knipe D M, Howley P, editors. Fields' virology. 4th edn. Philadelphia: Lippincott-Williams & Wilkins; 2001a. pp. 2731-2768; Oxman et al., 2005). The development of zoster may be viewed in the context of a continuum in immunodeficiencies, ranging from a natural decline in VZV-specific T cell immunity with age, to more serious immune deficiencies seen in cancer patients, organ transplant recipients, and ultimately in AIDS patients. Operationally defined as pain persisting for more than 4 to 6 weeks after zoster, PHN is the most common complication of zoster. PHN develops in >40% zoster patients over age 60 (200,000-300,000 Americans/year). Zoster patients also develop stroke from uni- or muli-focal vasculopathy, as well as myelitis and zoster paresis, retinitis and even pain without rash.

VZV is the first human herpesvirus for which a live-attenuated vaccine (OKA) is routinely administered to children in the USA (Arvin and Gershon, 1996). A more potent VZV vaccine has also been shown to reduce the incidence of zoster. An extensive study in 38,000 humans >60 years showed that zostavax vaccine reduced the number of zoster cases by 51% and the occurrence of PHN by 66% (Oxman et al., 2005). The FDA approved the vaccine for healthy adults >60 years. By the year 2030, it is estimated that 22% of the US citizens (65 million people) will be >65 years and by 2050, at least 21 million will be >85 years (Quan et al., 2007). Thus, in an ideal situation, even if every human >60 years were vaccinated, there would still be at least 500,000 zoster patients and almost half of whom will experience PHN. VZV myelitis and vasculopathy and possibly PHN are caused by persistent VZV infection (Gilden et al., Neuropathol. Appl. Neurobiol. 2011 August; 37(5):441-463).

OKA vaccine virus reactivates asymptomatically in vaccinated individuals (Krause and Klinman, 2000). Alternative strategies to develop new VZV vaccines include heat-inactivated as well as subunit vaccine (Breuer, 2006). Heat inactivated vaccine induces reduced class I-restricted killing of virus-specific lymphocytes (Hayward et al., Virol Immunol. 1996;9(4):241-5). Candidate zoster vaccines based on a recombinant (truncated) form of the VZV glycoprotein E (gE) boosts a pre-existing anti-gE humoral response (Vafai 1995). However, injection of mice with VZV gE peptides does not produce a strong humoral immune response (Breuer 2001). Such a vaccine is currently being tested with specific adjuvants as a target to boost cell-mediated immunity (Dendouga et al., 2012). A more efficient vaccine that induces a strong immune response but is less likely to reactivate is needed. In this context, a conditional varicella mutant (using a gene such as ORF 63 that is required for replication) can be used as a vaccine. Such a vaccine virus will provide a good humoral as well as cell-mediated immune response but would not reactivate to produce zoster.

Attempts to Produce VZV Infection in Animals.

VZV causes disease only in humans. Development of an experimental animal model that recapitulates the pathogenesis of VZV in humans is the goal of several laboratories. Corneal inoculation of mice (Wroblewska et al., 1993), intra-muscular inoculation of guinea pigs (Lowry et al., 1993; Tenser and Hyman 1987; Chen et al., 2003; Sadzot-Delvaux et al., 1990), and food pad inoculation of rats (Debrus et al., 1995; Kennedy et al., 2001) with VZV results in sero-conversion and virus entry into ganglia, confirmed by the detection of VZV DNA and RNA, without disease. VZV inoculation of human thymus and ganglionic implants under the kidney capsule of SCID-hu mice results in virus infection (Moffat et al., J. Virol. 1995 September;69(0):5236-42; Zerboni et al., Virology. 2005 Feb. 5;332(1):337-46). However, VZV reactivation has not been demonstrated in any of these models. Recently inoculation of cynomolgus monkeys with VZV has been shown to result in mild immune response without overt clinical symptoms although ganglia were not analyzed for the presence of latent VZV (Willer et al., J. Virol. 2012 April;86(7):3626-34).

Simian Varicella Virus (SVV) as a Model for Human VZV Disease.

Immunological, virological and pathological features of SVV infection of non-human primates closely resemble those of human VZV infection. Like VZV in humans, primary infection of primates with SVV leads to varicella followed by virus latency and spontaneous reactivation. Various non-human primate subspecies are susceptible to SVV infection (Gray, Rev. Med. Virol. 2004 November-December;14(6):363-81; Mahalingam and Gilden, In: Arvin A, Campadelli-Fiume G, Mocarski E, et al., editors. Human Herpesviruses: Biology, Therapy, and Immunoprophylaxis. Cambridge: Cambridge University Press; 2007; Chapter 58). SVV infection of rhesus macaques (RM) closely parallels VZV infection in humans, providing the best model of human VZV infection (Messaoudi et al., PLoS Pathog. 2009 November;5(11):e1000657). Primary SVV infection in monkeys results in viremia followed by rapid proliferation of both B and T cells (Ouwendijk et al., J. Neurovirol. 2012 April; 18(2):91-99; Ouwendijk et al., PloS Pathog. 2013 May;9(5):e1003368). SVV-specific IgG antibodies are detected at 10 dpi and peak at 17-19 days. Cell-mediated immune responses to SVV develop by day 7, with peak T cell counts seen at approximately 14 days (Messaoudi et al., 2009; Ouwendijk et al., 2012; Ouwendijk et al., 2013). Virus-specific T cell populations are a mixture of interferon-y-producing (effector) CD4+ T cells and $CD8^{+}$ T cells and appear early during the immune response in correlation with the development of SVV-specific antibodies. $CD8^{+}$ T cells have increased amounts of granzyme B, indicating cytotoxic potential (Messaoudi et al., 2009). After varicella, SVV becomes latent in ganglionic neurons (Kennedy et al. Virus Genes. 2004 April;28(3):273-6) at all levels of the neuraxis (Mahalingam et al, J. Virol. 2002 September;76(17):8548-8550). The present inventors have demonstrated SVV reactivation after social and environmental stress and after immunosuppression by irradiation, tacrolimus or prednisone (Mahalingam et al., Virology. 2007 Sep. 30;36(2):387-93; Mahalingam et al., J. Neurovirol. 2010 October;16(5):342-54). When SVV infection is disseminated, liver and lung are the most affected organs. Inflammation, hemorrhagic necrosis and eosinophilic intranuclear inclusions are seen in affected skin and viscera. SVV and VZV share immunological cross-reactivity. Sequence analysis of the complete SVV genome revealed 75% DNA homology with VZV (Gray et al., Virology. 2001 May 25;284(1):123-30). The complete SVV genome is available as a bacterial artificial chromosome (BAC) (Gray et al., Arch. Virol. 2011 May; 156(5):739-46). Point mutations can be introduced to elucidate the role of specific SVV genes in pathogenesis, latency and reactivation (Mahalingam et al., 2011).

Varicella ORF 63 Protein.

VZV ORF 63, which is present as a duplicate copy as ORF 70 on the VZV genome, is the most abundant transcript in latently infected human ganglia, and the protein is present in cytoplasm of infected neurons (Cohrs and Gilden, J. Virol 2007 March;81(6):2950-6; Mahalingam et al., Proc. Natl. Acad. Sci. U.S.A. 1996 Mar. 5;93(5):2122-4). A recent study of human ganglia latently infected with VZV has shown that the number of neurons expressing VZV ORF 63/70 protein during latency is much less than previously reported (Zerboni et al., J. Virol. 2010 April; 84(7):3421-3430). VZV ORF 63 protein is a component of the VZV tegument and represses both VZV as well as cellular promoters (Bontems et al., J. Biol. Chem. 2002 Jun. 7; 277(23):21050-60; Di Valentin et al., Biol. Chem. 2005 March; 386(3):255-67). VZV ORF 63/70 protein inhibits α-interferon-induced antiviral resonse in non-neuronal cells in culture (Ambagala and Cohen, J. Virol 2007 August; 81(15):7844-7851), alters the ability of human anti-silencing function 1 protein to bind histones (Ambagala et al., J. Virol. 2009 January; 83(1): 200-209), and inhibits neuronal apoptosis in cultured human ganglia (Hood et al., J. Virol. 2006 January; 80(2): 1025-1031). VZV ORF 63/70 protein binds to RNA polymerase II and VZV IE 62 and enhances VZV gI protomer activity (Lynch et al., Virology. 2002 Oct. 10;302(1):71-82). SVV ORF 63/70 shares 52% amino acid identity with VZV ORF 63/70 (Gray et al., 2001). Like VZV, SVV ORF 63/70 is also transcribed and translated in latently infected monkey ganglia (Mahalingam et al., 1996; Messaoudi et al., 2009). Recently, the inventors showed that while SVV ORF 63/70 is not essential for the development of cytopathic effect (CPE), productive replication of SVV lacking ORF 63/70 is impaired in Vero cells (Brazeau et al., J. Neurovirol. 2011 June; 17(3):274-280). These results, obtained using BAC constructs for the first time to examine this requirement of SVV ORF 63/70, were consistent with the findings of Cohen et al. 2004 in VZV (Cohen et al., J. Virol. 2004 November; 78(21):11833-11840). Cohen et al. 2004 purported but did not demonstrate that a VZV mutated to delete ORF 63 could afford advantages to current live VZV vaccines.

Therefore, notwithstanding the foregoing, there exists a great need for improved VZV vaccines, especially those which elicit long-lived protective immunity (ideally over an entire lifetime) and which are not subject to the virus sequestering in the ganglia and reactivating in susceptible individuals resulting in the onset of zoster or shingles. Also, because of the general problem of different herpesviruses becoming latent in specific cells of infected individuals, and viral infection reoccurring, e.g., in the case of HSV-1 and HSV-2, the problem of reoccurring oral or genital lesions, there is a great need for safe and effective herpesvirus vaccines, most especially for affording immuno protection against HSV-1 and HSV-2.

BRIEF SUMMARY

The present invention solves a substantial problem associated with currently available live VZV vaccines. Particularly, the present invention produces live VZV strains which, similar to current live VZV strains, when used to immunize susceptible individual to VZV infection and chickenpox, zoster or shingles elicits long-lived protective immunity, but unlike current live VZV strains used in vaccines, these mutated conditionally replication defective VZV strains are not susceptible to reactivation after becoming latent in ganglia.

The present invention particularly relates to the production of varicella virus conditional replication defective mutants, preferably ORF 63/ORF 70 mutants or ORF 62/71 mutants that only replicate under defined conditions. The invention further relates to the use of such mutants in vaccines in order to confer immunity against zoster or shingles. These conditional mutants which elicit long-lived protective immunity against the virus are ideally suited for use as a zoster or shingles vaccine because these mutants are not susceptible to virus reactivation, a cause of serious neurological disease, pain, blindness, paralysis and even morbidity in susceptible individuals.

More broadly the present invention provides mutated, recombinant live Herpesviridae strains, e.g., HSV-1, HSV-2, cytomegalovirus, human Varicella zoster virus, Epstein Barr virus, HHv-6a or HHV6b, HHV-7 or HHV-8, cells transfected therewith and live vaccines containing, wherein said mutated, recombinant live Herpesviridae strains only replicate under specific conditions (particular to the destabilization domain or gene) and which viral strains and vaccines containing afford long-lived immunity against the particular Herpesviridae strain when used to immunize an individual susceptible individual to infection; and further which mutated conditionally replication defective Herpesviridae strains are not susceptible to reactivation after becoming latent after in vivo administration.

Also, the invention provides methods of using such mutated, recombinant live Herpesviridae strains, e.g., HSV-1, HSV-2, cytomegalovirus, human Varicella zoster virus, Epstein Barr virus, HHv-6a or HHV6b, HHV-7 or HHV-8, and vaccines containing, for affording protective immunity against a Herpesviridae strain.

Further, the invention provides methods of boosting protective immunity against a particular Herpesviridae strain in an individual who previously has been inoculated with a vaccine containing a mutated, recombinant live Herpesviridae strains, e.g., HSV-1, HSV-2, cytomegalovirus, human Varicella zoster virus, Epstein Barr virus, HHv-6a or HHV6b, HHV-7 or HHV-8, by re-introducing conditions that provide for the conditional replication of said mutated, recombinant Herpesviridae strain, e.g., administration of an antibiotic, e.g., TMP.

Also, the invention provides combination vaccines and methods for the use thereof, said vaccines containing at least one mutated, recombinant live Herpesviridae strain according to the invention, e.g., HSV-1, HSV-2, cytomegalovirus, human Varicella zoster virus, Epstein Barr virus, HHv-6a or HHV6b, HHV-7 or HHV-8, and another virus or viral antigen, e.g., another Herpesviridae strain or a measles, mumps, diphtheria, or papillomavirus or an antigen thereof.

BRIEF DESCRIPTION OF EXEMPLARY OBJECTS AND EMBODIMENTS OF THE INVENTION

It is an object of the invention to produce variant or mutagenized viruses of the family Herpesviridae and host cells containing, which variants or mutagenized viruses are rendered conditionally replication defective by the incorporation or fusion of one or more destabilization domains onto viral genes which are essential for replication of the particular herpes virus. These variant or mutated Herpesviridae may be used in vaccines in order to provide protective immunity and further in order to prevent or reduce the potential for herpes virus reactivation in susceptible individuals.

The present invention embraces the creation of conditionally replication deficient Herpesviridae of any type. Such viruses may include Herpesviridae which infect humans and non-human animals. In preferred embodiments the variant or mutagenized Herpesviridae will preferably comprise Herpesviridae types that infect humans and which viruses are subject to reactivation after initial infection. These Herpesviridae viruses include in particular five species of Herpesviridae—HSV-1, which causes facial cold-sores, HSV-2 (which causes genital herpes), Varicella zoster virus, which causes chicken-pox and shingles, Epstein-Barr virus, which causes mononucleosis (glandular fever) and Cytomegalovirus. More particularly, there are 8 herpesvirus types which are known to infect humans: Herpes simplex viruses 1 and 2, varicella-zoster virus, EBV (Epstein-Barr virus), human cytomegalovirus, human herpesvirus 6, human herpesvirus 7, and Kaposi's sarcoma-associated herpesvirus (also known as human herpesvirus 8 or HHV/8).

However, the present invention contemplates the production of conditionally replication deficient Herpesviridae which infect animals as these strains conditionally, replication defective Herpesviridae strains will be useful in the agricultural industry and veterinary applications. In this regard there are more than 130 herpesviruses which infect different animals including mammals, birds, fish, reptiles, amphibians, and molluscs.

A common attribute of different herpes virus is their propensity to become latent in specific cell types after initial infection and to reactivate after the initial infection sometimes many years after the initial infection. For example, all of HSV-1, HSV-2 and VZV, for each of the primarily target cell is mucoepithelial cells, are all known to sequester or become latent in neurons. By contrast, HHV-4 or Epstein Barr virus for which the primary target cell is B cells and epithelial cells is known to become latent in B cells. HHV-5 or cytomegalovirus initially infects monocytes, lymphocytes and epithelial cells and may become latent in monocytes and lymphocytes after initial infection. The primary target cells for HHV-6 or Roseolovirus or herpes lymphotropic virus are T cells and this virus may become latent in such T cells after the initial infection. Similarly, the primary target cells for HHV-7 or Pityriasis Rosacea virus is T cells and this virus may become latent in the T cells in an infected individual many years after the initial viral exposure. Finally, the primary target cells for HHV-8 or Kaposi's sarcoma-associated herpesvirus or KSHV are lymphocytes (and some other cell types) and this virus may become latent in the B cells in an infected individual after the initial viral exposure.

Based on this common property of herpes viruses, this invention solves a problem associated with herpes viruses in general, namely the potential for reactivation after initial exposure. Specifically, this invention provides for the production of herpes viral vaccines containing mutated herpes viruses which are conditionally replication defective, which mutated herpes virus strains confer protection and which moreover, unlike existing vaccines and drugs, prevent or minimize the risk for subsequent viral reactivation, even many years after vaccination.

While the present invention is generic in nature, it is a specific object of the invention to provide mutated varicella viruses, preferably VZV that infect human and SVV that infects non-human primates. These mutant viruses replicate under defined conditions ("Conditional replication defective) as the result of the fusion of a destabilization domain to a gene required for virus replication, e.g., ORF 63, ORF 70, ORF 62 or ORF 71, wherein said mutants are still able to elicit protective immunity against SVV or VZV when administered in effective amounts vaccines and wherein the mutated viruses are not prone to reactivation, even after prolonged time (many years, e.g. 30, 40, 50 years or longer) in individuals vaccinated with vaccines containing said live mutated viruses.

It is another specific object of the invention to provide mutated HSV-1 or HSV-2 viruses, preferably HSV-2 mutant viruses which replicate under defined conditions ("Conditional replication defective) as the result of the fusion or insertion of at least one destabilization domain to a gene required for virus replication, e.g., DNA polymerase or another essential gene, wherein said HSV-1 or HSV-2 mutants are still able to elicit protective immunity against HSV-1 or HSV-2 when administered in effective amounts vaccines and wherein the mutated viruses are not prone to reactivation, even after prolonged time (many years, e.g. 30, 40, 50 years or longer) in individuals vaccinated with vaccines containing said live mutated viruses.

It is a more specific object of the invention to provide mutated varicella viruses, preferably VZV's that infect human and SVV that infects non-human primates. These mutants replicate under defined conditions ("conditionally replication defective") because of the fusion of a destabilization domain to ORF 63 or ORF 70 and the deletion or inactivation of the other copy of these genes by deletion, truncation or mutagenesis, wherein said mutants are still able to elicit protective immunity when administered as SVV or VZV vaccines and wherein the mutated viruses are not prone to reactivation in individuals vaccinated with said mutated viruses.

It is a another specific object of the invention to provide a recombinant human or primate varicella virus (e.g., VZV or SVV), wherein the genomic DNA of the virus is modified to produce a conditional replication deficient varicella vaccine strain, wherein the virus contains mutations selected from the following:
  (i) the virus comprises a mutated genome wherein gene 63 is deleted or inactivated by truncation or mutagenesis and gene 70 is fused to a destabilization domain:
  (ii) the virus comprises a mutated genome wherein gene 62 is deleted or inactivated by truncation or mutagenesis and gene 71 is fused to a destabilization domain:
  (iii) the virus comprises a mutated genome wherein gene 70 is deleted or inactivated and gene 63 is fused to a destabilization domain:
  (iv) the virus comprises a mutated genome wherein gene 71 is deleted or inactivated and gene 62 is fused to a destabilization domain:
  (v) the virus comprises a mutated genome wherein both gene 63 and gene 70 are fused to a destabilization domain:
  (vi) the virus comprises a mutated genome wherein gene 62 or gene 71 is fused to a destabilization domain and wherein said mutations to the viral genome recited in (i), (ii), (iii) or (iv) result in a conditionally replication deficient live varicella virus wherein the virus that only replicates under defined conditions.

In exemplary embodiments the virus will comprise a mutated OKA varicella vaccine strain, or a mutated simian varicella vaccine strain.

In exemplary embodiments the destabilization domain will comprise the *Escherichia coli* dehydrofolate hydroxylase (DHFR) destabilization domain.

In exemplary embodiments the destabilization domain is fused to the amino terminus of gene 70, and gene 63 is inactivated by deletion, truncation or mutagenesis.

In exemplary embodiments the destabilization domain is fused to the amino terminus of gene 63 and gene 70 is deleted or inactivated.

In exemplary embodiments the recombinant varicella virus may comprise a gene that encodes a detectable polypeptide, e.g., inserted at the site of deleted ORF 63 or ORF 70.

In exemplary embodiments the recombinant varicella virus may further comprise a gene that encodes a detectable polypeptide such as a green or red fluorescent polypeptide (GFP or RFP).

In exemplary embodiments the recombinant varicella virus may comprise a recombinant VZV or SVV which only replicates in the presence of the antibiotic trimethoprim (TMP).

In exemplary embodiments the invention further provides a cell transfected with a recombinant VV DNA according to the invention such as Vero (African monkey kidney) or other primate and human cell lines.

In exemplary embodiments the invention provides vaccines that elicit immunity against varicella virus, e.g., against VZV or SVV comprising an effective amount of a recombinant human or primate varicella-virus, wherein the genomic DNA of the virus is modified to produce a conditionally replication deficient varicella vaccine strain that elicits protection against the virus and which is not susceptible to reactivation in individuals vaccinated with said mutant varicella virus even after prolonged time (i.e., one or more decades after administration).

In exemplary embodiments the varicella viruses of the invention may be combined with other viral antigens such as VSV antigens or other viral vaccines such as mumps, measles, papilloma or diphtheria in order to produce a combined vaccine that elicits more potent anti-VZV immunity or a polyvalent vaccine which elicits protective immunity against different viruses.

In exemplary embodiments the vaccines of the present invention may be combined with conventional pharmaceutically acceptable carriers and excipients and optionally one or more immune adjuvants that potentiate Th1 immunity such as saponins, toll-like receptor (TLR) agonists, CD40 agonists, Saponin, ALUM and the like.

It is another object of the invention to provide novel methods of immunizing a susceptible mammal against varicella virus by administering an effective amount of a varicella virus which is not susceptible to reactivation after immunization, even years after administration, wherein the method comprises administering a vaccine comprising a therapeutically effective amount of a recombinant varicella virus according to the invention. In preferred embodiments the susceptible mammal will comprise a human or non-human primate.

In preferred embodiments the individual vaccinated will comprise a human who has not previously been immunologically exposed or developed immunity against VZV, e.g., an infant, child or adult.

In some embodiments the individual may be susceptible to VZV as a result of age, immune deficiency (such as via AIDS) or cancer.

In preferred embodiments the varicella viruses according to the invention are administered topically or by injection.

In exemplary embodiments the varicella vaccine of the invention is topically administered and the vaccine further comprises a topical carrier that facilitates by topical administration, e.g., to the skin, eye, oral cavity or lips, vaginal insertion or anal insertion.

It is another object of the invention to provide novel methods of immunizing a susceptible mammal against varicella virus by administering an effective amount of a varicella virus which is not susceptible to reactivation after immunization, even years after administration, wherein the method comprises administering a vaccine comprising a therapeutically effective amount of a recombinant varicella virus according to the invention, and the immunization regimen includes proximate (shortly before, simultaneous, or shortly after) to administration of the vaccine the additional administration of an agent that triggers the conditional replication of the virus, preferably the antibiotic trimethoprim.

It is another object of the invention to provide methods of constructing a recombinant varicella-zoster virus (VZV) or simian varicella virus according to the invention wherein the method comprises either (i) inactivating gene 63 by deletion, truncation or mutagenesis and optionally inserting another gene at the gene 63 loci in the viral genome and further inserting a nucleic acid encoding a destabilization domain at the amino terminus of gene 70 or (ii) inactivating gene 70 by deletion, truncation or mutagenesis and optionally inserting another gene at the gene 70 loci in the viral genome and further inserting a nucleic acid encoding a destabilization domain at the amino terminus of gene 63, or (iii) inserting a nucleic acid encoding a destabilization domain at the amino terminus of both gene 63 and gene 70 or gene 62 or gene 71, thereby producing a conditionally, replication deficient VZV or SVV strain that only replicates in the presence of an agent that inhibits the degradative effect of the destabilization domain on the gene 63, gene 70, or gene 62 or gene 71 polypeptide.

In exemplary methods, the destabilization domain comprises the *Escherichia coli* dihydrofolate hydroxylase (DHFR) destabilization domain and the resultant recombinant varicella virus only replicates in the presence of the antibiotic trimethoprim (TMP).

In exemplary embodiments the methods will comprise constructing a recombinant VZV using the genomic DNA of the OKA varicella vaccine strain which is mutated by the insertion of a DNA encoding the *E. coli* DHFR destabilization domain such that the 3' end of said fragment is fused to the 5' end of ORF 63 or ORF 70 and either ORF 70 or ORF 63 is deleted.

In exemplary embodiments the invention further provides a live vaccine containing an immunizing dose of the recombinant varicella-zoster virus according to the invention and stabilized forms thereof, e.g., freeze-dried vaccines.

In other exemplary embodiments the invention provides for the use of trimethoprim to boost immunity against the virus in individuals susceptible to zoster or shingles because of virus reactivation after the prior administration of a live vaccine containing an immunizing dose of the recombinant varicella-zoster virus according to the invention. These individuals may comprise older individuals (55+ years), and immunosuppressed individuals as the result of a disease such as HIV-AIDS or another disease affecting T and/or B cell immunity or individuals immunosuppressed as the result of disease treatment such as chemotherapy, radiotherapy, or other drugs that may impair T and B cell immunity such as methotrexate and drugs given before or after organ, tissue or cell transplant.

In other exemplary embodiments the invention provides mutated, recombinant Herpesviridae strain, wherein the corresponding wild-type Herpesviridae strain contains at least one gene that is essential for viral replication, and the mutated, recombinant Herpesviridae strain contains at least one of said genes which are essential for viral replication modified by the fusion or insertion of at least one destabilization domain, resulting in a conditionally replication deficient Herpesviridae strain that substantially only replicates under defined conditions specific to the inserted destabilization domain, preferably wherein the destabilization domain is the Escherichia DHFR destabilization domain and optionally wherein the destabilization domain is inserted or fused to at least 2 essential genes in the mutated, recombinant Herpesviridae strain, e.g., fused to the carboxy-terminus of at least one essential gene and/or fused to the amino-terminus of at least one essential gene. In preferred embodiments the mutated, recombinant Herpesviridae strain is selected from HSV-1, HSV-2, HHV-5 or Cytomegalovirus, HHV5 or Epstein Barr virus, HHV6A and HHV6B or herpes lymphotropic virus, Varicella-zoster virus, Simian varicella virus, HHV7 or Pityriasis Rosacea, and KSHV/HHV8.

In preferred embodiments the mutated, recombinant Herpesviridae strain is a mutated, recombinant HSV-1 strain wherein at least one of the following genes: DNA Polymerase (UL42), DNA Polymerase Catalytic Subunit (UL30), DNA Helicase (UL5), DNA Primase (UL52), ICP4 (transcriptional regulator), US1 (host range factor), UL49A (envelope protein), ICP0 (transcriptional regulator), UL1, UL8, UL9, UL14, UL15, UL17, UL18, UL19, UL22, UL25, U126, UL26.5, UL27, UL28, UL29 UL31, UL34, UL35, UL36, UL37, UL38, UL48, UL49, UL49.5, UL53, UL54, RS1, and/or US6 modified by the insertion or fusion of a destabilization domain thereto resulting in an HSV-1 strain that only replicates under inducible conditions specific to the destabilization domain.

In more preferred embodiments the mutated, recombinant Herpesviridae strain is a mutated, recombinant HSV-2 strain wherein at least one of the following genes: DNA Polymerase (UL42), DNA Polymerase Catalytic Subunit (UL30), DNA Helicase (UL5), DNA Primase (UL52), ICP4 (transcriptional regulator), US1 (host range factor), UL49A (envelope protein), ICP0 (transcriptional regulator), UL1, UL8, UL9, UL14, UL15, UL17, UL18, UL19, UL22, UL25, U126, UL26.5, UL27, UL28, UL29 UL31, UL34, UL35, UL36, UL37, UL38, UL48, UL49, UL49.5, UL53, UL54, RS1, and/or US6 modified by the insertion or fusion of a destabilization domain thereto resulting in an HSV-2 strain that only replicates under inducible conditions specific to the destabilization domain.

In other preferred embodiments the mutated, recombinant Herpesviridae strain is a mutated, recombinant HSV-1 strain wherein at least one of the following genes: DNA Polymerase (UL42), DNA Polymerase Catalytic Subunit (UL30), DNA Helicase (UL5), DNA Primase (UL52), and ICP4 (transcriptional regulator) are modified by the insertion or fusion of a destabilization domain thereto resulting in an HSV-1 strain that only replicates under inducible conditions specific to the destabilization domain.

In other preferred embodiments the mutated, recombinant Herpesviridae strain is a mutated, recombinant HSV-2 strain wherein at least one of the following genes: DNA Polymerase (UL42), DNA Polymerase Catalytic Subunit (UL30), DNA Helicase (UL5), DNA Primase (UL52), and ICP4 (transcriptional regulator) are modified by the insertion or fusion of a destabilization domain thereto resulting in an HSV-2 strain that only replicates under inducible conditions specific to the destabilization domain.

In other preferred embodiments the mutated, recombinant Herpesviridae strain is a mutated, recombinant Varicella-zoster virus or Simian varicella virus strain according to Claim 6, wherein at least one of the following genes: Gene or ORF 63/70 (host range factor), Gene or ORF 62/71, (transcriptional regulator) Gene or ORF 6 (DNA Primase), Gene 16, Gene or ORF 28 (DNA polymerase, DNA polymerase catalytic subunit), DNA Helicase ORF55, a DNA Packaging Protein encoding gene selected from ORF25, ORF26, ORF30, ORF34, ORF 42/45, ORF 43, ORF54, or an essential gene selected from ORF4, ORF5, ORF9A, ORF9, ORF17, ORF20, ORF21, ORF22, ORF24, ORF27, ORF29, ORF 31, ORF33, ORF 33.5, ORF37, ORF38, ORF 39, ORF 40, ORF41, ORF 44, ORF 46, ORF 48, ORF 50, ORF 51, ORF 52, ORF 53, ORF 56, ORF 60, ORF 61, ORF66, and/or ORF68 are modified by the insertion or fusion of a destabilization domain thereto resulting in an Varicella-zoster virus or Simian varicella virus strain that only replicates under inducible conditions specific to the destabilization domain.

In other preferred embodiments the mutated, recombinant Herpesviridae strain is a mutated, recombinant Varicella-zoster virus or Simian varicella virus strain according to Claim 6, wherein at least one of the following genes: Gene or ORF 63/70, Gene or ORF 62/71, (transcriptional regulator) Gene or ORF 6 (DNA Primase), Gene 16, Gene or ORF 28 (DNA polymerase, DNA polymerase catalytic subunit), and DNA Helicase ORF55, are modified by the insertion or fusion of a destabilization domain thereto resulting in an Varicella-zoster virus or Simian varicella virus strain that only replicates under inducible conditions specific to the destabilization domain preferably human varicella zoster virus strain.

In other preferred embodiments the mutated, recombinant Herpesviridae strain is a mutated, recombinant HHV-5 or cytomegalovirus strain wherein at least one of the following genes DNA Polymerase (UL54), DNA Helicase (UL105), UL79, UL87, UL95, DNA Primase (UL70), UL91, UL84, UL77, UL44, IE1 and/or IE2 are modified by the insertion or fusion of a destabilization domain thereto resulting in an HHV-5 or cytomegalovirus strain that only replicates under inducible conditions specific to the destabilization domain.

In other preferred embodiments the mutated, recombinant Herpesviridae strain is a mutated, recombinant HHV-5 or cytomegalovirus strain according to Claim 6, wherein at least one of the following genes DNA Polymerase (UL54), and DNA Helicase (UL105), are modified by the insertion or fusion of a destabilization domain thereto resulting in an HHV-5 or cytomegalovirus strain that only replicates under inducible conditions specific to the destabilization domain.

In other preferred embodiments the mutated, recombinant Herpesviridae strain is a mutated, recombinant HHV-4 or Epstein Barr virus strain wherein at least one of the following genes DNA Polymerase (BORF2), DNA Helicase (BBLF4), DNA Primase (BSLF1), BXLF1, EBNA-1, and/or EBNA-2 are modified by the insertion or fusion of a destabilization domain thereto resulting in an HHV-5 or cytomegalovirus strain that only replicates under inducible conditions specific to the destabilization domain.

In other preferred embodiments the mutated, recombinant Herpesviridae strain is a mutated, recombinant HHV-4 or Epstein Barr virus strain wherein the DNA Polymerase (BORF2) is modified by the insertion or fusion of a destabilization domain thereto resulting in an HHV-4 or Epstein Barr virus strain that only replicates under inducible conditions specific to the destabilization domain.

In other preferred embodiments the mutated, recombinant Herpesviridae strain is a mutated, recombinant HHV6A and HHV6B or herpes lymphotropic virus strain wherein at least one of the following genes: DNA Polymerase, Glycoprotein Q1, DNA Helicase, DNA Primase, and/or U27 are modified by the insertion or fusion of a destabilization domain thereto resulting in an HHV6A and HHV6B or herpes lymphotropic virus strain that only replicates under inducible conditions specific to the destabilization domain.

In other preferred embodiments the mutated, recombinant Herpesviridae strain is a mutated, recombinant HHV6A and HHV6B or herpes lymphotropic virus strain wherein at least one of the following genes: DNA Polymerase, Glycoprotein Q1 are modified by the insertion or fusion of a destabilization domain thereto resulting in an HHV6A and HHV6B or herpes lymphotropic virus strain that only replicates under inducible conditions specific to the destabilization domain.

In other preferred embodiments the mutated, recombinant Herpesviridae strain is a mutated, recombinant HHV7 or Pityriasis Rosacea viral strain wherein at least one of the following genes: DNA polymerase, DNA Helicase, DNA Primase, and/or U26 are modified by the insertion or fusion of a destabilization domain thereto resulting in an HHV7 or Pityriasis Rosacea viral strain that only replicates under inducible conditions specific to the destabilization domain.

In other preferred embodiments the mutated, recombinant Herpesviridae strain is a mutated, HHV7 or Pityriasis Rosacea viral strain wherein at least the DNA Polymerase gene is modified by the insertion or fusion of a destabilization domain thereto resulting in an HHV7 or Pityriasis Rosacea viral strain that only replicates under inducible conditions specific to the destabilization domain.

In other preferred embodiments the mutated, recombinant Herpesviridae strain is a mutated, recombinant KSHV/HHV8 viral strain wherein at least one of the following genes: DNA polymerase, DNA Helicase, DNA Primase, and/or ORF57 are modified by the insertion or fusion of a destabilization domain thereto resulting in an KSHV/HHV8 viral strain that only replicates under inducible conditions specific to the destabilization domain.

In other preferred embodiments the mutated, recombinant Herpesviridae strain is a mutated, KSHV/HHV8 viral strain wherein at least the DNA Polymerase gene is modified by the insertion or fusion of a destabilization domain thereto resulting in a KSHV/HHV8 viral strain that only replicates under inducible conditions specific to the destabilization domain.

In other preferred embodiments any of the mutated, recombinant Herpesviridae strains according to the invention is in a vaccine composition that comprises an effective amount of at least one mutated recombinant Herpesviridae strain according to any one of Claims 1-20, wherein the effective amount comprises an amount of the virus sufficient to confer protective immunity in a susceptible host, and further comprising a pharmaceutically acceptable carrier or excipient, optionally containing at least one immune adjuvant, e.g., a cytokine, TLR agonist, saponin, ALUM, or another known adjuvant.

In other preferred embodiments the mutated, recombinant Herpesviridae strain is in a combination or multivalent vaccine that affords immunity against at least one Herpesviridae strain and another virus e.g., another Herpesviridae strain or a non-herpesvirus such as a mumps, rubella, tetanus, diphtheria, human papilloma, or measles virus or a combination thereof.

In other preferred embodiments the mutated, recombinant Herpesviridae strain is contained in a mammalian cell that has been transfected with at least one mutated, recombinant Herpesviridae strain, or a culture comprising a transfected mammalian cells In other preferred embodiments the invention provides a method for electing protective immunity against at least one Herpesviridae strain, which comprises the following steps:

(i) administering to a host that is susceptible to infection by a particular Herpesviridae strain a vaccine that comprises an effective amount of said particular Herpesviridae strain which comprises at least one mutated recombinant Herpesviridae strain which mutated strain contains at least one destabilization domain fused or inserted into at least one gene which is essential for the replication of said particular containing said mutated particular Herpesviridae strain administering to the susceptible host Herpesviridae strain; and (ii) before, concomitant or after the administration of said vaccine, further administering to said host at least one compound that results in the conditional expression of the essential gene or genes which contain or are fused to at least one destabilization domain, sand allowing the virus to replicate for a sufficient time to allow the susceptible host to develop protective immunity against the particular Herpesviridae strain. In preferred embodiments the destabilization domain comprises the *Escherichia coli* DHFR destabilization domain and the compound that results in conditional viral replication comprises TMP.

In other preferred embodiments the invention provides a method for boosting protective immunity in an individual who has been previously vaccinated against a Herpesviridae strain using a mutated Herpesviridae strain which comprises administering to said individual at least one compound that results in the conditional expression of the essential gene or genes which are contained in or are fused to at least one destabilization domain resulting in the expression of said at least one essential gene and the replication of said mutated Herpesviridae strain, and allowing the Herpesviridae virus to replicate for a sufficient time to allow the individual to boost their protective immunity against the particular Herpesviridae strain e.g., wherein the destabilization domain is the *E. coli* DHFR destabilization domain and wherein boosting is effected by the administration of TMP, and/or the individual is over 40 years old, is immunocompromised, or has cancer or HIV infection. In preferred embodiments in these methods the Herpesviridae strain comprises HSV-1 or HSV-2 or the Herpesviridae strain comprises human varicella zoster or the Herpesviridae strain comprises HHV4 or Epstein Barr virus or the Herpesviridae strain comprises HHV5 or cytomegalovirus or the Herpesviridae strain comprises HHV7 or Pityriasis Rosacea virus or the Herpesviridae strain comprises KSHV/HHV8 or the Herpesviridae strain comprises HHV6A, HHV6B or herpes lymphotropic virus.

DESCRIPTION OF THE FIGURES

FIG. 6 shows that the lowest amount of TMP that can be used with SVV mutant 2 is $5 \times 10^{-2}$ µM.

FIG. 7 shows the effect of TMP on the replication of SVV mutant 2 is reversible. SVV mutant 2-infected Vero cells were cultured in the presence of 100 nM TMP and active virus replication was confirmed by the detection of GFP expression (before TMP removal). The virus was passaged two rounds on Vero cells in the absence of TMP. Minimal GFP expression was detected (after TMP removal). TMP (100 nM) was added again to the culture and GFP expression returned to the original levels (TMP added back).

FIG. 11 schematically depicts experiments involving the experimental inoculation of SVV mutant 2 and SVV EGFP. In the experiments, four Indian rhesus macaques are divided into two groups. In each group, one of the monkeys is treated with 3.3 mg/kg of TMP for 3 days. The monkeys are then inoculated intrabronchially with either SVV mutant 2 (group 1) or SVVEGFP (group 2). The monkeys are sacrificed on 14 dpi and tissues are collected for analysis.

FIG. 12 shows the genomes of wild type and mutant SVV in which EGFP and the bacmid vector sequences have been removed. Also, in the mutant SVV, ORF63 has been replaced with RFP (red fluorescent protein)

FIG. 13 shows reduction in number of mutant SVV plaques with reduced quantities of TMP. Single plaque at 10 nM TMP was barely visible.

FIG. 14 contains the results of an experiment demonstrating that the effect of TMP on mutant SVV replication is reversible.

FIG. 17 contains the results of an experiment wherein SVV-seronegative rhesus macaques were inoculated with mutant SVV in the presence or absence of 20 mg/kg of TMP did not show rash or viremia.

FIG. 18 shows the structure and the cytopathic effect produced by the new SVV mutant in which DHFR was fused at the C-terminal end.

FIG. 19 contains the results of an experiment demonstrating that TMP is required for efficient replication of the new SVV mutant and that the effect is reversible.

FIG. 20 shows a mutant SVV (dd63-DHFRfused at the C-terminal end), and the results of an experiment which revealed that this mutant grows better than another SVV mutant (ud63-DHFR fused at the N-terminal end).

FIG. 21 shows the genome of mutant HSV-1 in which DHFR is fused to the essential DNA polymerase gene at the N-terminal end.

FIG. 22 shows the reduced number of plaques with the HSV-1 mutant in the absence of TMP. The cells with wild type HSV were blown away by infection (data not shown).

Detailed Description of Preferred Embodiments

Before disclosing the invention in detail the following definitions are provided. Otherwise the words and phrases herein should be accorded their ordinary meaning as they would be understood by one skilled in the art.

DEFINITIONS

"Adjuvant" refers to any moiety that enhances Th1 immunity against an antigen, herein a herpesvirus such as VZV, HSV-1 or HSV-2 when combined with the live Herpesviridae, e.g., VZV, HSV-1 and HSV-2 vaccines of the present invention.

"BAC" refers to a recombinant bacterial artificial chromosome (BAC).

"Conditionally Replication Defective Virus or VZV or SVV" refers to a virus that has been mutated such that one or more genes involved and required for viral replication are only expressed under conditional (induced) conditions. Preferably it is achieved by the insertion or fusion (to the C- or N-terminus) of a destabilization domain gene "Destabilization domain" refers to a polypeptide encoded by a nucleic acid which when fused to the coding sequence of a polypeptide such as a viral replication gene causes the polypeptide to be degraded unless a particular condition is met (e.g., presence of an antibiotic) which prevents or inhibits the degradation otherwise elicited by the destabilization domains. Preferably the domain is linked at or proximate to the 5' end of a Herpesviridae gene involved in replication, e.g., VZV or SVV gene 62, gene 63, gene 70 or gene 71 or other Herpesviridae genes listed in Table 1 infra.

"Dosage effective amount" in the context of the invention refers to an amount of a mutated conditionally replication deficient Herpesviridae strain, e.g., an VZV or HSV-1 or HSV-2 strain according to the invention that confers immunity against the particular Herpesviridae strain, which amount of virus is obtained when the conditionally replication defective mutant Herpesviridae strain is exposed to conditions that provide for the replication of the mutated virus. In exemplary embodiments the inducible conditions that permit replication comprise the administration of the antibiotic trimethoprim which when administered proximate to the mutated strain or even years after vaccine administration results in the replication of the sequestered virus and thereby the initial generation of protective immunity or the boosting of protective immunity against a particular Herpesviridae strain, e.g., a protective immune response against VZV and/or the prevention of chicken pox, zoster or shingles or protection against HSV-1 or HSV-2, and the protection against later outbreaks in an individual in need thereof, e.g., an infant, child, teenager or adolescent or an adult, including those susceptible to zoster, shingles, HSV-1, HSV-2 or another Herpesviridae strain as the result of advanced age, stress, sexual contact, or immunosuppression because of a particular disease such as HIV-AIDS or cancer or a treatment regimen such as chemotherapy, radiotherapy or drugs given to prevent rejection of transplanted organs, tissues or cells. The effective amount of the mutated Herpesviridae viral strain required for effective initial protection or immune boosting may vary given the particular strain, or weight and heath of the individual treated.

"*Escherichia coli* DHFR destabilization domain" or "*Escherichia coli* DHFR destabilization gene" refers to a sequence derived from the *E. coli* dihydrofolate reductase (DHFR) polypeptide which when fused (to the C- or N-terminus of the polypeptide) or incorporated into proteins such as viral genes encoding polypeptides involved or required for viral replication may cause degradation of the protein unless an effective amount of the sulfa antibiotic trimethoprim or an equivalent is present. (See Iwamoto et al., 2010).

The sequence of exemplary DHFR destabilization domain nucleotide and protein sequences are contained in SEQ ID NO: 1 and 2 preceding the claims. Preferably the DHFR destabilization domain will comprise a polypeptide at least 80% identical to SEQ ID NO: 2, more preferably at least 85% identical, still more preferably at least 90% identical and even more preferably at least 95, 96, 97, 98 or 99% identical thereto.

"Gene essential to viral replication" or "Gene essential to herpesvirus replication" herein refers to a gene present in a virus, e.g., a herpesvirus, the expression of which alone or in association with another viral gene is required for the virus to replicate and maintain its normal life cycle. Herpesviruses have been well studied, in particular those that infect humans, and there are a number of genes in each of Herpes simplex viruses 1 and 2, varicella-zoster virus, EBV (Epstein-Barr virus), human cytomegalovirus, human herpesvirus 6, human herpesvirus 7, and Kaposi's sarcoma-associated herpesvirus (human herpesvirus 8) which have been identified to be essential to virus replication. Examples of such genes are disclosed infra in Table 1.

"Herpesviridae" herein or herpesviruses refers to a large family of DNA viruses that cause diseases in animals, including humans. The members of this family are also known as herpesviruses. The family name is derived from the Greek word herpein ("to creep"), referring to the latent, recurring infections typical of this group of viruses. Herpesviridae can cause latent or lytic infections. There are more than 130 herpesviruses, and some are from mammals, birds, fish, reptiles, amphibians, and mollusks.

Figure 1:
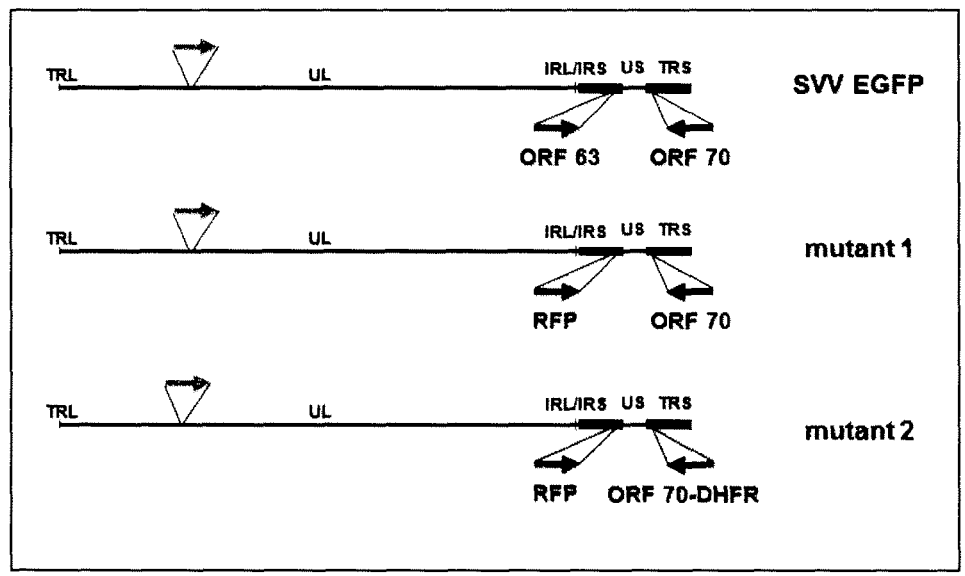
FIG. 1 schematically depicts the construction of SVV mutants. Using an SVV (bacterial artificial chromosome) BAC containing EGFP-tagged SVV genome (SVV-EGFP), two mutants were produced. In mutant 1, SVV ORF 63 was replaced with red fluorescent protein. In mutant 2, in addition to deletion of SVV ORF 63, ORF 70 was fused at the N-terminus with a destabilizing domain (purple line) that, upon translation, will lead to degradation of ORF 70 protein.

Of these there are 8 known herpesvirus types: Herpes simplex viruses 1 and 2, varicella-zoster virus, EBV (Epstein-Barr virus), human cytomegalovirus, human herpesvirus 6, human herpesvirus 7, and Kaposi's sarcoma-associated herpesvirus. Of these 8, there are at least five species of Herpesviridae which are extremely widespread among humans, HSV-1, which causes facial cold-sores, HSV-2 (genital herpes), Varicella zoster virus, which causes chicken-pox and shingles, Epstein-Barr virus, which causes mononucleosis (glandular fever) and Cytomegalovirus—which are extremely widespread among humans. More than 90% of adults have been infected with at least one of these, and a latent form of the virus remains in most people.

"PHN" refers to postherpetic neuralgia (PHN).

"Simian varicella virus or SVV" is the simian counterpart of VZV and like VZV is a neurotropic alphaherpesvirus which causes varicella in simians and like VZV virus becomes latent in ganglia along the entire neuraxis, and may reactivate during immunosuppression resulting in zoster like symptoms.

"Substantially arrests or stops" viral gene expression refers to the conditional blocking of the expression of a particular gene, i.e., a viral gene required for virus replication by the insertion or fusion of a destabilization domain thereto, e.g., E. coli DHFR destabilization domain. By "substantially arrest, stops or block" means that the polypeptide encoded by the essential gene is not expressed, or expressed at very low levels compared to the expression levels in the absence of the destabilization domain when inducible conditions specific for the destabilization domain are absent. Generally gene expression is reduced by at least 90%, 95% or 99% relative to the expression of the gene in a wild-type strain. This may be referred to alternatively as "leaky expression".) In preferred embodiments the gene is not expressed at all when inducible conditions are absent. This may be achieved in some instances by the fusion of the destabilization domain to different essential genes, such as at the 5' or 3' end thereof.

"Substantially arrests or stops viral replication" refers to the impeded, reduced or arrested rate of replication of a viral mutant, preferably a herpesvirus mutant containing at least one destabilization domain inserted or fused to at least one gene essential for viral replication, when inducible conditions (specific to the destabilization domain) are not present. In preferred embodiments the virus will not replicate at all when inducible conditions are not present, or will replicate at very reduced levels compared to the wild-type strain, i.e., the rate of replication will be at most 5% of the wild-type, more preferably at most 1% of the wild-type stain replication and even more preferably at most 0.1% of the replication rate of the wild-type strain. (This may be referred to alternatively as "leaky expression".) Viral replication may be totally blocked in some instances by the incorporation of several destabilization domains, incorporated or fused onto several genes essential for viral replication.

"Varicella zoster virus (VZV)", is an exclusively human neurotropic alphaherpesvirus, causes chickenpox in children after which virus becomes latent in ganglia along the entire neuraxis, and which may reactivate in susceptible individuals, particularly immunocompromised as the result of age, stress, disease or treatment regimen resulting in zoster or shingles.

DETAILED DESCRIPTION

As disclosed supra, this invention provides novel and improved live herpes viruses including by way of example mutated varicella zoster and herpes simplex virus -1 and -2, and viral vaccines which contain these viruses which are mutated such that they only replicate under defined (induced) conditions.

In the present invention a particular herpes virus which infects humans or non-human animals is mutated by the incorporation or fusion of a destabilization domain onto one or more genes of the virus which are essential for viral replication. As a result of the destabilization domain the virus only replicates under controlled or inducible conditions. Upon initial vaccination with such recombinant herpes virus the individual is exposed to the inducible conditions, i.e., an antibiotic which effectively turns on the replication gene and allows the virus to replicate. Thereby, the host is permitted to be exposed to a sufficient amount of the virus and the viral antigens for the development of protective immunity. After such protective immunity is attained the inducible conditions are removed and the virus, including virus that becomes sequestered or latent in specific cells is unable to replicate.

As described infra, the present application contains working examples with 3 different herpes viruses VZV, SVV and HSV-1, the results of which establish that the incorporation of a destabilization domain onto at least one gene which is essential for viral replication is an effective means of creating a mutated viral strain that substantially is only capable of replication under inducible conditions.

In the case of both VZV and SVV this is accomplished by the incorporation or fusion of the destabilization domain onto ORF 63 or 70. This may be accomplished by the incorporation or fusion of the destabilization domain at the 5' or 3' end of the gene, or at a site within the 63 or 70 genes or proximate to the 5' or the 3' terminus thereof.

In the case of HSV-1 or HSV-2 this may be accomplished by the incorporation or fusion of the destabilization domain onto any one or several of the essential genes DNA Polymerase (UL42), DNA Polymerase Catalytic Subunit (UL30), DNA Helicase (UL5), DNA Primase (UL52), ICP4 (transcriptional regulator), ICP0 (transcriptional regulator), US1 (host range factor), UL49A (envelope protein), or other HSV-1 or HSV-2 genes which are essential for viral replication. The identity of different herpesvirus genes which reportedly are essential for the replication of different herpesviruses is known in the art. In addition, Table 1 infra enumerates such genes for different herpesviruses. This list is intended to be exemplary and not exhaustive.

This may be accomplished by the incorporation or fusion of the destabilization domain at the 5' or 3' end of one or more genes essential for virus replication, e.g., in HSV-1 or HSV-2 at a site within the DNA polymerase and/or ICP4 genes or proximate to the 5' or 3' terminus of another essential viral gene.

In producing particular mutated herpesviruses according to the invention the placement of the one or more destabilization domain will depend upon the particular genes of the particular herpesvirus which alone or in combination are essential for replication. As noted above, herpesviruses and the genes which are involved in or are essential for virus replication has been well studied.

A table listing different herpes viruses and the particular genes that are essential or very important for viral replication are listed in Table 1 below. This Table should be considered to be exemplary and not exhaustive as alternatively the destabilization domain may be incorporated into other genes involved in viral replication.

TABLE 1

LISTING OF HERPESVIRUSES AND GENES THAT CAN BE USED FOR VACCINE PREPARATION

| TYPE OF HERPES VIRUS | DISEASE ASSOCIATED THERWITH | FIRST OPTION | SECOND OPTION |
|---|---|---|---|
| HSV-1 | Cold sores | DNA Polymerase (UL42) DNA Polymerase Catalytic Subunit (UL30) DNA Helicase (UL5) DNA Primase (UL52) ICP4 (transcriptional regulator) | USI (host range factor) UL49A (envelope protein) ICP0 (transcriptional regulator) Other Essential Genes including UL1, UL8, UL9, UL14, UL15, UL17, UL18, UL19, UL22, UL25, Ul26, UL26.5, UL27, UL28, UL29 UL31, UL34, UL35, UL36, UL37, UL38, UL48, UL49, UL49.5, UL53, UL54, RSI, US6 |
| HSV-2 | Genital and oral Herpes | DNA Polymerase (UL42) DNA Polymerase Catalytic Subunit (UL30) DNA Helicase (UL5) DNA Primase (UL52) ICP4 (transcriptional regulator) | ICP0 (transcriptional regulator) US1 (host range factor) UL49A (envelope protein) Other Essential Genes UL1, UL8, UL9, UL14, UL15, UL17, UL18, UL19, UL22, UL25, Ul26, UL26.5, UL27, UL28, UL29, UL31, UL34, UL35, UL36, UL37, UL38, UL48, UL49, UL49.5, UL53, UL54, RS1, US6 |
| Varicella-zoster virus Simian varicella virus | Chicken pox or shingles. | Gene or ORF 63/70 (host range factor) Gene or ORF 62/71 (transcriptional regulator) Gene or ORF 6 (DNA Primase) Gene 16, 28 (DNA polymerase, DNA polymerase catalytic subunit) DNA Helicase ORF55 | DNA Packaging Proteins ORF25, ORF26, ORF30, ORF34, ORF 42/45, ORF 43, ORF54 Other Essential VZV Genes ORF4, ORF5, ORF9A, ORF9, ORF17, ORF20, ORF21, ORF22, ORF24, ORF27, ORF29, ORF 31, ORF33, ORF 33.5, ORF37, ORF38, ORF 39, ORF 40, ORF41, ORF 44, ORF 46, ORF 48, ORF 50, ORF 51, ORF 52, ORF 53, ORF 56, ORF 60, ORF 61, ORF66, ORF68 |
| HHV-5 or Cytomegalovirus | Salivary gland infection, infectious Mononucleosis-like syndrome, retinitis. | DNA Polymerase (UL54) DNA Helicase (UL105) | UL79 UL87 UL95 DNA Primase (UL70), UL91, UL84, UL77, UL44, 1E1 1E2 |
| HHV-4 or Epstein-Barr Virus | Infectious Mononucleosis or glandular fever, Burkitt's syndrome, CNS lymphoma in AIDS patients, post-transplant lymphoproliferative syndrome, nasopharyngeal carcinoma, HIV-associated hairy leukoplakia. | DNA Polymerase (BORF2) | DNA Helicase (BBLF4), DNA Primase (BSLF1), BXLF1, EBNA-1, EBNA-2 |
| HHV6A and HHV6B or herpes lymphotropic virus | | DNA Polymerase Glycoprotein Q1 | DNA Helicase, DNA Primase, U27 |

TABLE 1-continued

LISTING OF HERPESVIRUSES AND GENES THAT CAN BE
USED FOR VACCINE PREPARATION

| TYPE OF HERPES VIRUS | DISEASE ASSOCIATED THERWITH | FIRST OPTION | SECOND OPTION |
| --- | --- | --- | --- |
| HHV7 or Pityriasis Rosacea | Roseola infantum or exanthema subitum | DNA Polymerase | DNA Helicase, DNA Primase, U26 |
| KSHV/HHV8 | Kaposi's sarcoma, primary effusion lymphoma, some types of multicentric Castleman's disease. | DNA Polymerase | DNA Helicase, DNA Primase, ORF57 |

"Varicella zoster virus (VZV)", is an exclusively human neurotropic alphaherpesvirus, causes varicella (chickenpox) in children, after which virus becomes latent in ganglia along the entire neuraxis. VZV reactivation in elderly individuals, immunocompromised organ transplant recipients, and patients with cancer and AIDS produces zoster (shingles) and chronic pain (postherpetic neuralgia [PHN]), paralysis (VZV myelitis), stroke (VZV vasculopathy), and blindness (VZV retinitis). Zoster develops in ~1 million Americans each year. By the year 2030, 22% of US citizens (65 million people) will be >65-yrs-old, and by 2050, at least 21 million people will be >85-yrs-old (Quan et al., 2007). While OKA varicella vaccine reduces the incidence of zoster by 51% over a 3-year period, even if every person >60 yrs old were vaccinated, there would still be at least 500,000 zoster patients annually, of whom ~40% would experience PHN. There is therefore a need for a varicella vaccine for use in humans that induces a long-lasting immune response and not reactivates and cause zoster.

Clinical, immunological, pathological, and virological analysis reveals that simian varicella virus (SVV) infection of primates is the counterpart of VZV infection in humans. Experimental SVV infection of monkey's produces varicella, after which virus becomes latent, and immunosuppression of latently infected monkeys produces zoster (Mahalingam et al., 2007; 2010). The SVV and VZV genomes encode open reading frame (ORF) 63, which is duplicated in the terminal repeat region as ORF 70.

As disclosed in the Background of the Invention, the present inventors have shown that, like VZV ORF 63/70, SVV ORF 63/70 expression is required for SVV replication in culture. VZV ORF 63 inhibits the α-interferon-induced antiviral response in non-neuronal cells in culture (Ambagala and Cohen, 2007), alters the ability of human anti-silencing function 1 protein to bind histones (Ambagala et al., 2009), and inhibits neuronal apoptosis in cultured human ganglia (Hood et al., 2006). Also, DNA polymerase expression is required for HSV-1 and HSV-2 replication.

These data provided a rationale for the inventors' hypothesis that a vaccine containing a varicella virus conditional mutant deficient in ORF 63 or ORF 70 expression or potentially a conditional mutant conditionally deficient in ORF 62 or ORF 71 expression will elicit long-lived immunity against the virus without being prone to reactivation, even years after virus administration. More broadly, this data provided a rationale for the inventors' hypothesis that a vaccine containing a live conditionally replication defective Herpesviridae virus, i.e., one wherein at least one gene essential for replication contains or is fused to a destabilization domain will elicit long-lived immunity against the virus without being prone to reactivation, even years after virus administration.

As disclosed in detail in the experimental examples infra, the present inventors, initially using a recombinant bacterial artificial chromosome (BAC) containing the EGFP-tagged SVV genome, generated two mutants. In mutant 1, SVV ORF 63 was replaced with red fluorescent protein. In mutant 2, in addition to deletion of SVV ORF 63, ORF 70 was fused at the N-terminus with a destabilizing domain that, upon translation, led to degradation of ORF 70 protein. However, in the presence of the antibiotic trimethoprim (TMP), ORF 70 protein was stable and promoted virus replication. The inventors further determined the minimum quantity of TMP required for active replication in culture to be 10 nM and that the effect of TMP on the replication of mutant 2 in culture is reversible.

These results suggested that these conditional SVV or analogous VZV mutants and potentially other conditionally replication deficient herpesviruses can be administered in a vaccine in association with the antibiotic TMP (before, simultaneous, or after virus administration) and that this combination will elicit a protective immune response or boost protective immunity against the virus and further that replication of the virus may be reversibly completely "turned off" by the removal of the antibiotic. This is highly significant as these results suggest that the inventive mutated varicella viruses, and potentially other conditionally replication deficient herpesviruses even after prolonged latency in ganglia or other cells after in vivo administration, should not be capable of reactivation unless the conditional stimulus (TMP) is present. Accordingly, the present inventors reasonably believe that vaccines containing these conditional VZV viral mutants should be capable of preventing zoster or shingles, and potentially that other conditionally replication deficient herpesviruses will protect against the particular herpesvirus and should not be subject to reactivation.

As further described below and in the examples which follow, in order to further corroborate the efficacy of an exemplified conditional SVV mutant (referred to as mutant 2) the preparation and use of which is disclosed infra for use as a vaccine, the time point post-infection for mutant 2 at which protective adaptive SVV-specific immunity is established may be determined. Four groups of SVV-seronegative Indian rhesus macaques are inoculated intrabronchially with mutant 2. Three of the groups are treated with TMP from −3 to +3 days post infection (dpi), −3 to +6 dpi, and −3 to +12 dpi, respectively. All four groups of monkeys are challenged at 30 dpi by intrabronchial inoculation with 105 plaque-forming units of wild type SVV. Bronchial alveolar lavage (BAL) and blood samples are collected at multiple dpi and days post challenge (dpc). Blood, skin, lung and ganglia are collected from euthanized monkeys at the expected peaks for the adaptive immune response (14 dpc) and latency (60 dpc). Viral loads are determined from BAL and blood by cocultivation, and wild type- and mutant-specific PCR. SVV-specific B- and T-cell immunity is determined by FACS analyses. Tissues are examined by immunohistochemistry (IHC), in situ hybridization (ISH), and virus-specific PCR to determine the dpi at which SVV-specific immunity is achieved.

In addition, the role of SVV ORF 63 expression in reactivation from latency in monkeys may be confirmed. In these experiments two groups of SVV-seronegative Indian rhesus macaques are inoculated intrabronchially with mutant 2. Both groups are treated with TMP at −3 to +12 dpi and immunosuppressed two months later. One of the groups is treated with TMP starting 3 days before immunosuppression, and both groups are examined for rash as well as subclinical reactivation by analyzing blood, ganglia, and lung by PCR, reverse transcriptase PCR (RT-PCR), and IHC. The mutated SVV virus should be less or not subject to reactivation.

The experiments embodied in some of the examples are conducted using the simian varicella virus rather than human varicella zoster virus. As is known to those skilled in the art, these herpesviruses comprise very similar genomes including ORF 63 and 70, and these genes for both of these herpesviruses are essential for virus replication. Also, both simians and humans are susceptible to the virus latent in ganglia and reactivating resulting in rash or shingle like symptoms. Accordingly results in the simian system are predictive and establish a reasonable likelihood of success using an analogous conditional replication deficient human varicella virus mutant, i.e., VZV mutant wherein either ORF 63 or ORF 70 is deleted or otherwise inactivated by mutation or truncation and the remaining ORF 63 or ORF 70 is rendered conditionally defective as a consequence of it being fused to a destabilization domain.

The examples herein use SVV as a model for human VZV further since analogous experiments cannot ethically be conducted in humans. However, based on the high degree of sequence identity of the ORF63 and ORF70 polypeptides in primate SVV and human VZV strains, because of the fact that in both species these genes are required for replication and reactivation, and that for both SVV and VZV the viruses are prone to reactivation after establishing latency in ganglia, particularly during immunosuppression, and thereupon result in similar pathology known as shingles or zoster, SVV is a perfect model to study the efficacy of a putative human VZV vaccine.

Essentially, the inventive human VZV vaccine will preferably comprise an effective amount of a live varicella human vaccine in which ORF 63 or ORF 70 expression (or potentially ORF 62 or gene 71 or another essential replication gene) is conditionally blocked as the result of a destabilization domain fused thereto, and the remaining gene copy of ORF 63 and ORF 70 which is not fused to a nucleic acid encoding such destabilization domain, i.e., either ORF 70 or ORF 63, is either deleted or otherwise inactivated such as by truncation or mutagenesis, resulting in a live viral vaccine that confers long-lived protective immunity but which virus does not reactivate, even after prolonged duration after sequestration of the virus in the ganglia.

In some of the working examples ORF 63 or ORF 70 is deleted. However, alternatively, one skilled in the art can readily determine whether a specific truncation or mutation of the ORF 63 or ORF 70 gene which is not fused to a destabilization domain is effective to eliminate viral replication. Generally, at least 25% of the gene will be deleted; more preferably at least 50%, 75% or 90% of the gene will be deleted. Similarly, one skilled in the art can determine whether another mutation inactivates ORF 63 or ORF 70, such as the insertion of another sequence such as nonsense codons, or other sequences which preclude translation of a functional ORF 63 or ORF 70. However, in the most preferred embodiments the ORF 63 or ORF 70 gene contained in the recombinant virus which is not fused to the destabilization domain is substantially or entirely deleted so as to minimize any risk of reactivation in the absence of the conditional stimuli, e.g., as a consequence of viral gene rearrangement or mutagenesis over time.

As noted above, in some embodiments both copies of the replication genes, i.e., both ORF 63 and ORF 70 may be fused to a destabilization domain. This should still prevent viral reactivation and may facilitate the virus replicating under appropriate conditions (trimethoprim administration) to produce a viral titer in vivo that is sufficient that generate a protective immune response. However, in preferred embodiments either ORF 63 or ORF 70 will be inactivated by deletion, truncation or mutation and either ORF70 or ORF63 will be fused to a nucleic acid encoding a destabilization domain.

The information and data contained in this application provides a reasonable expectation that VZV strains, e.g., OKA strains that conditionally express only one copy of ORF 63 or ORF 70 should elicit protective immunity and should not be subject to reactivation. In addition, VZV strains, e.g., OKA strains that conditionally express ORF 62 or 71 based on fusion thereof to a destabilization domain should also elicit protective immunity when the virus is permitted to replicate under inducible conditions (TMP present) and similarly should not be subject to reactivation as ORF 62 and ORF 71 are absolutely required for VZV replication.

Therefore, based on the foregoing, the invention provides novel and improved mutated VZV strains as well as other mutated Herpesviridae strains, methods for their manufacture, and methods for their use in vaccines which, when administered in conjunction with trimethoprim should reduce or even eliminate serious neurologic disease caused by VZV, or another herpesvirus, particularly in the rapidly increasing elderly and immunocompromised populations such as cancer patients, HIV-AIDS patients and other individuals who are immunocompromised as the result of disease or therapeutic regimen such as drug therapy, chemo or radiotherapy or drugs used during organ or tissue transplantation.

Based on the results herein the inventors contemplate that a preferred dosage of trimethoprim to be used in association with the subject vaccines will comprise 15-20 mg/kg per day (i.e., 70 μmoles/kg/day) This antibiotic is preferably administered shortly before the vaccine is administered, e.g., within several hours or a day prior, and/or is administered concurrent or shortly after (within several hours or a day) after the vaccine is administered.

The VZV or other Herpesviridae vaccine and the antibiotic may be in the same or separate compositions. Preferably they are separate as the mode of administration of these moieties may be different, e.g., the antibiotic may be administered orally and the virus by injection, typically intravenous, intramuscular, subcutaneous, or topically, or intranasally.

As mentioned, the subject VZV and other mutated Herpesviridae strain containing vaccines may be used in infants, children, teens and adolescents or in adults of all ages to confer protective immunity against zoster or shingles or against another herpesvirus. In some preferred embodiments the VZV or other herpesvirus vaccine and antibiotic are administered to infants or children to prevent shingles or against later infection with the particular herpesvirus later in life. However, in other preferred embodiments the vaccine containing the mutated herpesvirus and antibiotic may be administered to adults prone to developing zoster or shingles or another herpesvirus infection because of age, immunodeficiency or immunosuppression, e.g., as a result of cancer, HIV-AIDS, cancer, or disease treatment such as chemotherapy, radiotherapy or another drug that causes immunosuppression such as methotrexate or drugs given to individuals undergoing organ, tissue or stem cell transplant or cell therapy.

In addition, the invention contemplates the use of trimethoprim to in effect function as a "booster vaccine" in individuals who have been vaccinated with VZV or against another herpesvirus such as HSV-1 or HSV-2 but who are at risk of developing zoster or shingles or herpes outbreak because of immunosuppression as the result of advanced age, disease, stress or therapeutic regimen. In such individuals the subject viral strains in the presence of the TMP antibiotic may reactivate and thereby replicate and boost immunity against the virus and thereby prevent the onset of zoster or shingles.

As mentioned, the present approach is applicable to any varicella zoster virus strain or other herpesvirus that causes disease that is prone to reactivation after becoming latent in the ganglia or other cells after in vivo administration. In the case of VZV this includes in particular the OKA strain, a strain well known in the art, for example as disclosed in Arbeter et al. (Journal of Pediatrics, vol 100, No 6, p 886), WO9402596, and U.S. Pat. No. 3,985,615. Any other suitable live attenuated VZV strain may also be used in the invention. For example, the Varilrix and Varivax strains are both appropriate and commercially available and could be employed in the invention.

The subject mutated conditionally replication defective VZV or analogous other conditionally replication deficient herpesvirus strain strains may be administered alone or with other actives. For example, the vaccine may further comprise an isolated VZV or other herpesvirus antigen or immunogenic derivative thereof, suitably being a purified VZV or other herpesvirus antigen. Also, the subject vaccines may contain conventional stabilizers, excipients, and potentially adjuvants that boost the anti-viral Th1 immune response elicited against the live virus. Adjuvants are well known and available.

Also, the subject VZV or other herpesvirus vaccine compositions may be multivalent, i.e., they may be combined with other attenuated live viruses or combined with viral antigens such as those conventionally used in mumps, measles, diphtheria, tetanus, papillomavirus or other viral vaccines.

In some embodiments the subject live VZV viral vaccine may be combined with a VZV antigen such as the gE antigen (also known as gp1), or immunogenic derivatives thereof. The gE antigen, anchorless derivatives thereof (which are also immunogenic derivatives) and production thereof is described in EPO405867 and references therein [see also Vafai A. Antibody binding sites on truncated forms of varicella-zoster virus gpI (gE) glycoprotein Vaccine 1994 12:1265-9]. EP192902 also discloses gE and production thereof. Other suitable antigens which may be included in the subject VZV zoster or shingles vaccine include, by way of example, gB, gH, gC, gI, IE63 (e.g. see, Huang et al. J. Virol. 1992, 66: 2664, Sharp et al. J. Inf. Dis. 1992, 165:852, Debrus, J. Virol. 1995 May; 69(5):3240-5 and references therein), IE62 (e.g. see Arvin et al. J. Immunol. 1991 146:257, Sabella J. Virol. 1993 December; 67(12):7673-6 and references therein) ORF4 or ORF 10 (Arvin et al. Viral Immunol. 2002 15: 507.)

The present invention also contemplates that antigen combinations may be used with the subject live conditionally replication defective VZV, such as gE with IE63, or gE with IE62, for example.

In another aspect the invention relates to the combination of the TMP antibiotic and the VZV strain or another herpesvirus strain, e.g., OKA strain, and optionally a VZV or other herpesvirus antigen for concomitant or sequential administration, in any order. Where delivery is concomitant the 2 components are delivered in the same or different compositions, which may be administered by different routes such as oral, injection or topical administration. Injection includes in particular intravenous, intramuscular or subcutaneous delivery of the virus strain.

Adjuvants which may be combined with the subject mutated conditionally replication deficient VZV or other mutated herpesvirus strains include immunostimulants such as but not limited to detoxified lipid A from any source and non-toxic derivatives of lipid A, saponins and other reagents, suitably capable of stimulating a TH1 type response.

Suitable adjuvant systems which promote a predominantly Th1 response include, Monophosphoryl lipid A or derivatives thereof such as 3-de-O-acylated monophosphoryl lipid A. It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of Bacterial Eendotoxins, Plenum Publ. Corp., NY, p 407-419). A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof. 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants which optionally may be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, Int. Arch. Allergy. Immunol., 79(4):392-6; Hilgers et al., 1987, Immunology, 60(1):141-6; and EP 0 549 074 B1). In one aspect the bacterial lipopolysaccharide adjuvant is 3D-MPL. Other LPS derivatives that optionally may be used as adjuvants in the vaccines of the present invention are immunostimulants with a similar structure to that of LPS or MPL or 3D-MPL. These LPS derivatives may be an acylated monosaccharide, which is a sub-portion to the above structure of MPL.

Saponins are described in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., Crit. Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B 1. Other saponins which have been used in systemic vaccination studies include those derived from other plant species such as *Gypsophila* and *Saponaria* (Bomford et al., Vaccine, 10(9):572-577, 1992). An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739. In one aspect the combination of QS21 with 3D MPL is used in the present invention.

A particularly potent adjuvant formulation involving QS21 and 3D-MPL in an oil in water emulsion is described in WO 95/17210 and is also suitable for use in the present invention.

An alternative adjuvant choice is an unmethylated CpG dinucleotides ("CpG"). CpG is an abbreviation for cytosine-guanosine dinucleotide motifs present in nucleic acid. CpG oligonucleotides are disclosed in WO 96/02555 and EP 468520. Also, other toll-like receptor (TLR) agonists potentially may be used as adjuvants in the subject VZV and other herpesvirus vaccine formulations according to the invention.

The present invention also provides a method for producing kits suitable for inducing an immune response against zoster or other herpesvirus infection, the method comprising mixing a mutated VZV or another mutated herpesvirus virus according to the invention, together with an adjuvant or adjuvant combination, and combining in a kit along with an effective dosage of the antibiotic trimethoprim sufficient to induce viral replication and protective immunity upon administration.

The amount of VZV or other mutated herpesvirus used in the subject VZV or other herpesvirus vaccine is an amount which induces an immunoprotective response without significant, adverse side effects. For the OKA strain, for example, reported suitable doses include 1350 pfu of Oka/Merck VZV vaccine for children and 18,700-60,000 pfu of Oka/Merck vaccine for healthy adults older than 60. These same or similar doses can be employed for other strains (see Quan et al., 2007). It is anticipated that the subject conditionally mutated VZV strains may be administered at about the same or higher dosages, e.g., on the order of 2-fold to 10-fold higher than conventional VZV dosages because the replication of the subject VZV virus strains are impaired compared to the parent strain by virtue of the loss or inactivation of one of the genes involved in replication and/or the fusion of the destabilization domain to the other viral gene involved in replication An optimal amount for a particular vaccine can be ascertained by standard studies involving observation of appropriate immune responses in subjects. Following an initial vaccination, subjects may receive one or several booster immunizations adequately spaced. The composition(s) of the present invention may be formulated for any appropriate manner of administration, including for example, topical, oral, nasal, mucosal, intravenous, intradermal, intraperitoneal, subcutaneous and intramuscular administration. Delivery of the OKA strain is, in one aspect, by subcutaneous delivery.

The immunogenic composition of the present invention may be used in a vaccine composition, optionally in combination with another active, an adjuvant and/or (other) suitable carrier. The VZV of the present invention, optionally a VSV antigen and an adjuvant may be used together in a composition to provoke an immune response to VZV, or separately—either concomitantly or sequentially in a prime boost regime. For concomitant or sequential delivery the components of the vaccine may be used in either order. In one embodiment, delivery of a live conditionally replication defective mutant VZV according to the invention may be followed by administration of a VZV antigen or immunogenic derivative thereof. In another embodiment delivery of a VZV antigen or immunogenic derivative thereof is followed by delivery of the inventive mutated live conditionally replication deficient VZV.

The invention further relates to a method of preventing and/or decreasing the severity of herpes zoster and/or post herpetic neuralgia comprising delivering to a seronegative individual at risk of zoster an immunogenic composition comprising a live conditionally replication deficient VZV according to the invention.

In a further embodiment the invention relates to a method of preventing and/or decreasing the severity of herpes zoster and/or post herpetic neuralgia comprising sequential or concomitant delivery to a seronegative individual at risk of zoster of a live mutated VZV according to the invention optionally in combination with a VZV antigen such as gE.

For example, a prime boost regime in humans comprises, in one aspect, priming with 25-100 μg gE, in one aspect 40-100 μg gE, such as 50 or about 50 μg gE, or an immunogenic derivative thereof, adjuvanted with QS21 (for example QS21 quenched with cholesterol as described above) and 3D-MPL, and boosting with the inventive conditional replication defective mutated strain of VZV, such as OKA.

Where prime boost regimes are used, or where multiple vaccination regimes are used, then 2, 3, 4 or more immunizations may be employed. Suitable regimes for prime boost include 1, 2, 3, 4, 5 or 6 months between individual immunizations.

A prime boost schedule comprises, in one aspect, delivery of a VZV antigen or immunogenic derivative thereof, suitably an adjuvanted VZV antigen or derivative, at 0 months and boosting with a live VZV according to the invention at 2M.

In an alternative delivery schedule there is concomitant delivery of both of the two individual components (VZV antigen or derivative) and live conditionally mutated attenuated VZV) at both 0 and 2 months.

The invention further relates to use of a the subject mutated live VZV strain in the preparation of a combination vaccine further containing a VZV antigen for the prevention of herpes zoster, and to use of a VZV antigen and the subject mutated live VZV strain in the preparation of a combination vaccine for the prevention of herpes zoster.

In another embodiment a VZV antigen such as the gE antigen, or immunogenic derivative or immunogenic fragment thereof, may be used with an adjuvant to enhance the efficacy of the subject live VZV vaccine. That is, the gE antigen or immunogenic derivative or immunogenic fragment thereof may be used as an immune potentiator in a vaccination schedule that includes administration of the subject conditionally replication deficient VZV strains in order to further enhance eliciting a protective anti-VZV immune response.

The subject conditionally replication defective VZV strains preferably may be used in the preparation of a medicament for the prevention or amelioration of herpes zoster reactivation and/or post herpetic neuralgia. The composition or vaccine is suitably used in the population of seronegative people 50 or older than 50. Suitably the population is the population of those older than 55, 60, 65, 70, 75, 80, or older than 80. Suitably the population is 50-70 years. In one aspect the population of individuals is those who have had varicella or who have had a live varicella vaccine.

Thus the invention relates to use of a composition as described above in the preparation of a medicament for the prevention or amelioration of herpes zoster reactivation and/or post herpetic neuralgia in a population of people 40, 50 or above. The invention thus also relates to a method for the prevention or amelioration of herpes zoster reactivation and/or post herpetic neuralgia, the method comprising delivering to a seronegative individual in need thereof a vaccine composition of the invention.

Methods for preparing vaccines using live viruses or viral antigens are known in the art. For example, vaccine preparation is generally described in New Trends and Developments in Vaccines, Voller et al. (eds), University Park Press, Baltimore, Md., 1978. It is anticipated that the subject conditionally replication defective mutant VZV strains may be formulated, dosed and administered substantially in accord with reported formulation, dosage and administration protocols which are efficacious with other known and commercially available attenuated VZV live virus vaccines.

The forgoing description should be sufficient to teach one of skill in the art how to practice the invention as embodied in the claims. The invention is further described by the following, non-limiting Examples.

EXAMPLES

Example 1

Construction of Recombinant SVV BAC Clone Containing a Conditional ORF 63/70 Mutant To prepare SVV ORF 63/70 mutants, the inventors used an SVV BAC containing the complete SVV genome and sequences that encode EGFP driven by the CMV immediate-early promoter (Gray et al., 2011). To introduce mutations into SVV ORF 63/70, the two-step red-mediated mutagenesis protocol developed by Tischer et al., (2006) was used.

The details of the protocol have been described (Brazeau et al., 2011). Briefly, as shown in FIG. 1 we prepared 2 SVV mutant BACs using an SVV BAC containing EGFP-tagged SVV genome (SVV-EGFP). In mutant 1, SVV ORF 63 was replaced with red fluorescent protein. In mutant 2, in addition to deletion of SVV ORF 63, ORF 70 was fused at the N-terminus with a destabilizing domain (purple line) that, upon translation, will lead to degradation of ORF 70 protein. This is also shown schematically in FIG. 2.

More specifically, to prepare mutant 1, a recombinant clone was used that contained sequences that encode RFP (red fluorescent protein) interrupted by the kanamycin gene (kindly provided by Dr. Benedikt Kaufer, Freie Universität Berlin, Germany). Using oligonucleotide primers containing sequences upstream or downstream of SVV ORF 63/70 at the 5'-end and RFP-specific sequences at the 3'-end, resulted in amplification of a 1748 by DNA fragment. This DNA fragment was used to transform E. coli GS1783 containing wild-type SVV BAC. Kanamycin-resistant colonies were selected and extracted with recombinant BAC DNA and analyzed by Hind III digestion and agarose gel electrophoresis. Afterward the kanamycin cassette was eliminated. Complete replacement of SVV ORF 63 sequences by RFP was confirmed by sequence analysis as shown in FIG. 1, mutant 1).

To prepare mutant 2, a recombinant DNA clone was used containing the destabilization domain derived from E. Coli dihydroxyfolate reductase (DHFR) (kindly provided by Dr. Thomas Wandless, Stanford University, CA (nucleic acid and polypeptide sequences for this destabilization domain are contained in SEQ ID NO:1 and 2), and introduced the kanamycin-cassette at a unique restriction site (PmeI) within the sequences encoding the destabilization domain. As described above, this was effected by PCR amplification and transformation of E. coli GS1783 containing SVV BAC mutant 1. After elimination of the kanamycin cassette, mutant SVV BAC (mutant 2) in which the destabilization domain was fused at the amino terminus of SVV ORF 70, was obtained. Proper fusion of the DHFR destabilization domain to the SVV ORF 70 was confirmed by sequence analysis.

Accordingly, in summary these example 2 SVV mutants were constructed using an SVV BAC containing EGFP-tagged SVV genome (SVV-EGFP. In mutant 1, SVV ORF 63 was replaced with red fluorescent protein. In mutant 2, in addition to deletion of SVV ORF 63, ORF 70 was fused at the N-terminus with a destabilizing domain (purple line) that, upon translation, will lead to degradation of ORF 70 protein.

Example 2

Preparation of Infectious Recombinant SVV from BAC Clones

Figure 3:
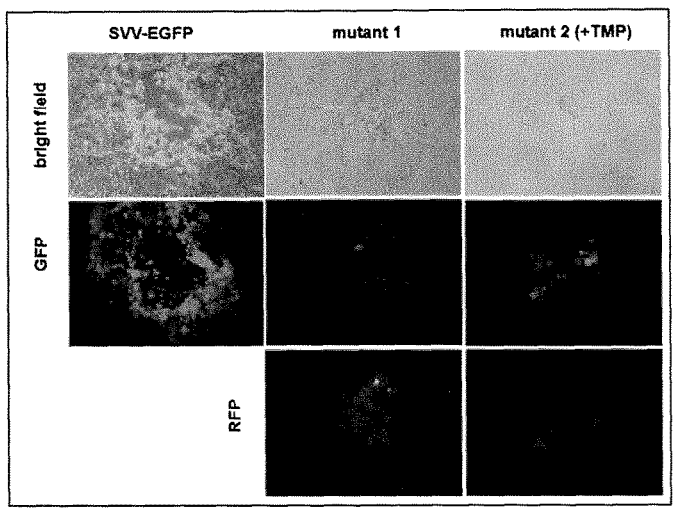
FIG. 3 depicts the preparation of SVV ORF 63/70-conditional mutant virus. In the experiments therein. BACs contacting SVV-EGFP, mutants 1 and 2 were transfected into Vero cells. TMP (10 µM) was used after transfection of mutant 2 BAC. Bright field images of the CPE associated with the viruses are presented. Expression of GFP and RFP associated with the CPE were visualized by green and red fluorescence.

This example relates to the experiments depicted in FIG. 3. This figure shows the preparation of SVV ORF 63/70-conditional mutant virus. As described below, BACs contacting SVV-EGFP, mutants 1 and 2 (FIG. 1) were transfected into Vero cells. TMP (10 µM) was introduced after transfection of mutant 2 BAC. The bright field images of the CPE associated with the viruses were then evaluated wherein the expression of GFP and RFP associated with the CPE were visualized by green and red fluorescence.

Figure 2:
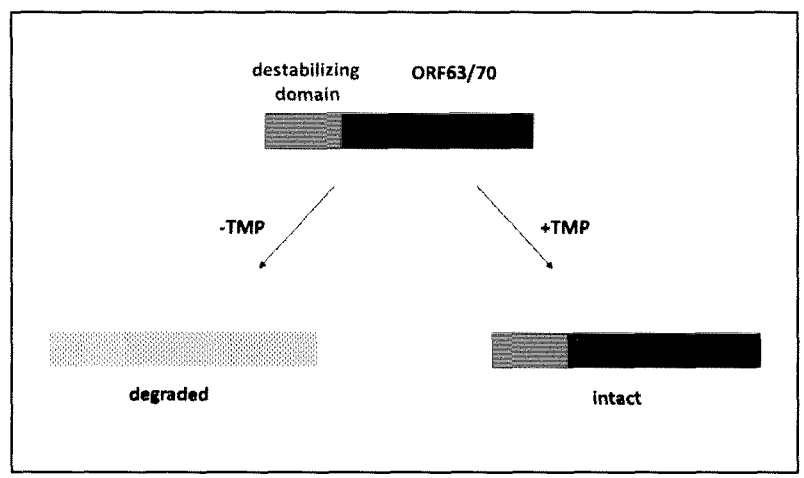
FIG. 2 schematically shows the fusion of a destabilization domain to ORF 63/70 and further depicts that in the absence of trimethoprim (TMP) the ORF 63/70 polypeptide is degraded because of the effect of the destabilization domain whereas in the presence of TMP the ORF 63/70 polypeptide required for effective viral replication remains intact.

The experiments revealed that the transfection of SVV BAC containing EGFP into Vero (African monkey kidney) cells in culture produced a cytopathic effect (CPE) that was visualized by the expression of green fluorescence (FIG. 2; SVV-EGFP). Transfection of SVV BAC containing EGFP and RFP in place of ORF 63 (mutant 1) into Vero cells in culture produced a CPE that was visualized by both green and red fluorescence (FIG. 3; mutant 1).

Figure 4:
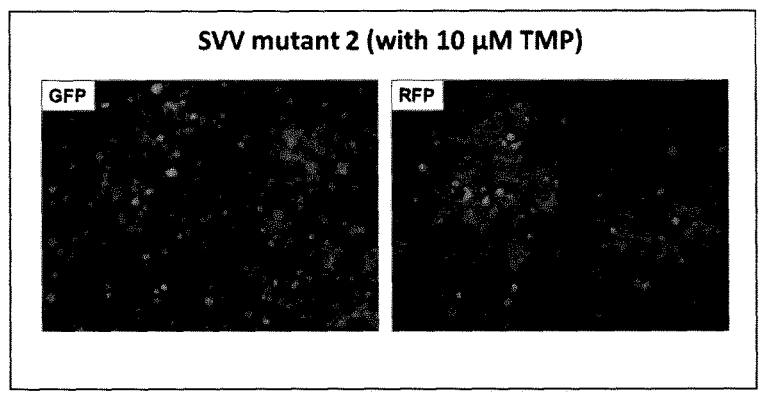
FIG. 4 contains the results of an experiment showing that both RFP and GFP are expressed in SVV mutant 2 infected Vero cells in the presence of 10 micromolar TMP.

It was determined that 10 µM TMP was not toxic to Vero cells or rhesus fibroblasts in culture. Transfection of SVV BAC containing EGFP and RFP in place of ORF 63 and the destabilizing domain fused to SVV ORF 70 (mutant 2) into Vero cells and cultured in the presence of 10 µM TMP produced a CPE that was also visualized by both green and red fluorescence [FIG. 3, mutant 2(+TMP)]. In addition, FIG. 4 contains the results of an experiment revealing that both RFP and GFP are expressed in SVV mutant 2 infected Vero cells in the presence of 10 µM TMP. (As mentioned, in the experiments the SVV ORF 63/70 regions from the DNA extracted from SVV-EGFP, mutants 1 and 2 virus-infected cells were PCR amplified and complete replacement of ORF 63 by RFP in mutant 1 and proper fusion of the destabilization domain to ORF 70 were confirmed by sequence analysis).

We further are characterizing the rate of growth of the mutated viruses in the presence and absence of TMP (experiments ongoing)

Example 3

Minimum Quantity of TMP Needed for Productive Replication of Mutant 2

Figure 5:
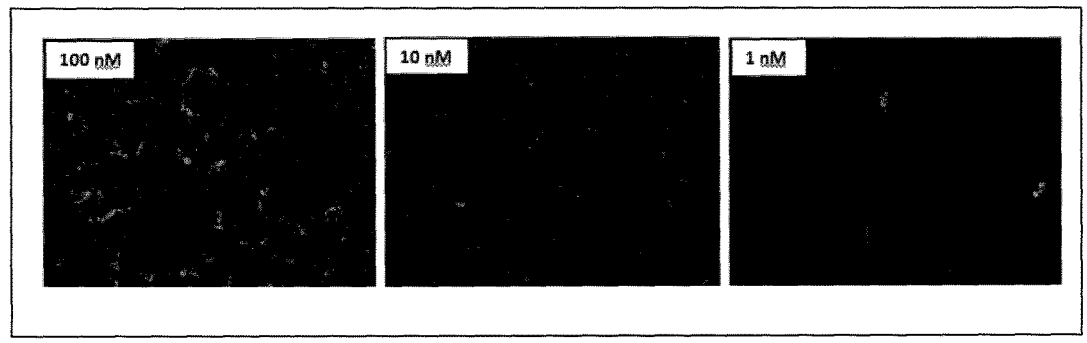
FIG. 5 shows the effect of the dose of TMP on replication of SVV mutant 2. Infection of Vero cells with SVV mutant 2 was done at 100, 10 and 1 nM of TMP in the tissue culture medium. GFP expression was monitored using an inverted microscope. Virus-specific cpe was present at 100 and 10 nM TMP but not at 1 nM TMP.

Vero cells were infected with mutant 2 in the presence of 10-fold dilutions of TMP. Replication of mutant 2 was monitored by GFP expression (FIG. 5). Active replication of mutant 2 was seen in medium containing 100 and 10 nM TMP. However, no virus replication was seen at 1 nM TMP. Thus, the minimum quantity of TMP needed for replication of mutant 2 is 10 nM. In these experiments the effect of the quantity of TMP on replication of SVV mutant 2 and the infection of Vero cells with SVV mutant 2 was done at 100, 10 and 1 nM of TMP in the tissue culture medium. GFP expression was monitored using an inverted microscope. The results showed that virus-specific CPE was present at 100 and 10m nM TMP but not at 1 nM TMP. In addition, the experiments contained in FIG. 6 with decreasing amounts of TMP show that the lowest amount of TMP that can be used with SVV mutant 2 is $5 \times 10^{-2}$ µM.

Example 4

Reversibility of the Effect of TMP on Mutant 2

To determine whether the effect of TMP on the replication of SVV mutant 2 is reversible SVV mutant 2-infected Vero cells were cultured in the presence of 100 nM TMP and active virus replication was confirmed by the detection of GFP expression (before TMP removal). The virus was passaged two rounds on Vero cells in the absence of TMP. Minimal GFP expression was detected (after TMP removal). TMP (100 nM) was added again to the culture and GFP expression returned to the original levels (TMP added back).

Figure 8:
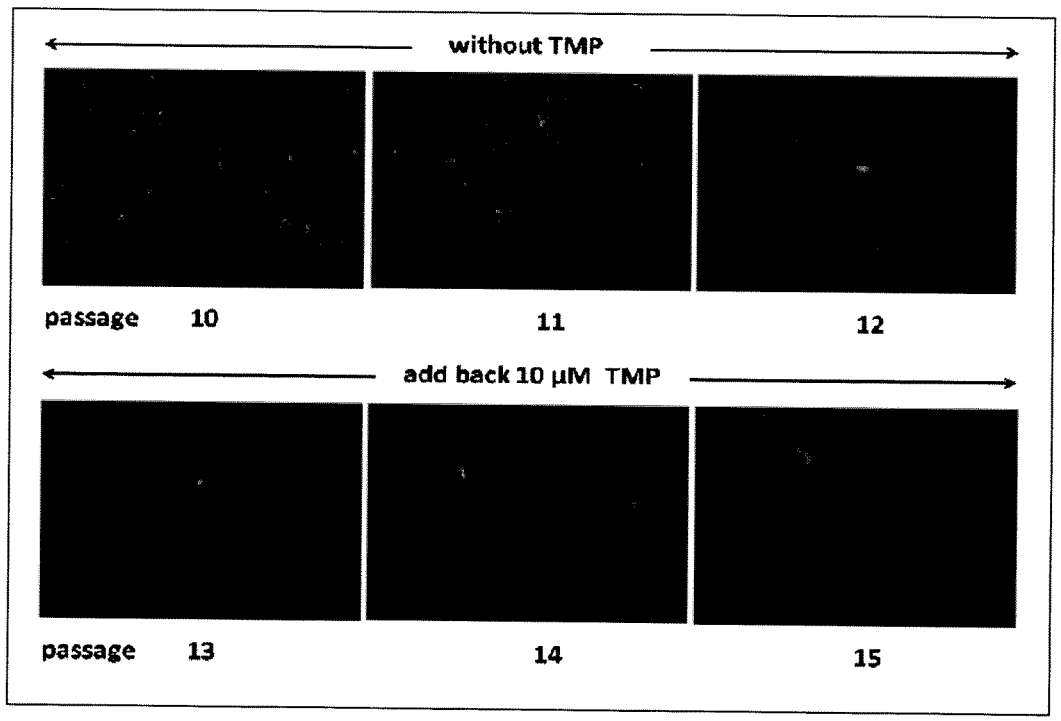
FIG. 8 (fluorescence assay) and FIG. 9 (bright field assay) contain the results of similar experiments which show that the effect of TMP on the SVV mutant 2 strain is reversible.
Figure 9:
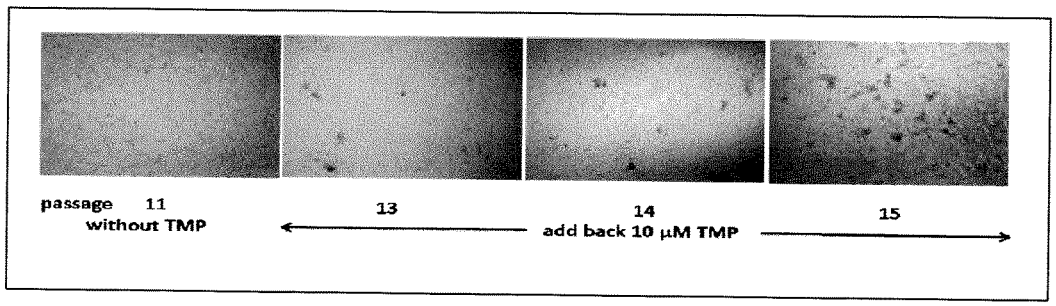

The results of these experiments are in FIG. 7. In these experiments which were intended to determine if the effect of TMP on the replication of mutant 2 is reversible, the virus was passaged two rounds without TMP. It was observed that that the GFP expression was considerably reduced indicating the absence of active virus replication. However, addition of TMP in the culture resulted in the recovery of GFP expression indicating active virus replication (FIG. 7). In addition, FIG. 8 (fluorescence assay) and FIG. 9 (bright field assay) contain the results of similar experiments which show that the effect of TMP on the SVV mutant 2 strain is reversible Accordingly, the cumulative data suggest that the effect of TMP on virus replication is reversible.

Example 5

Analysis of BAL and Immune Cells in SVV Infected Monkeys

In collaboration with Dr. Georges Verjans (Department of Virology, Erasmus Medical Center, The Netherlands), the inventors also performed experiments that showed that primary SVV infection of Chinese rhesus macaques leads to ganglionic infection and the induction of a virus-specific adaptive B- and T-cell memory response in the absence of skin rash (Ouwendijk et al., 2012). African green monkeys, when infected with the viruses were found to develop a more pronounced viremia during acute SVV infection, with wild type (wt) SVV (269 and 279) or SVV-GFP (273,283,294), (i.e. SVV mutant containing GFP gene but lacking destabilization domain fused to gene 63 or gene 70). All animals developed varicella rash starting 7-8 dpi, which were macroscopically identified as GFP-positive fluorescent varicella lesions in multiple organs including skin and tongue of SVV-GFP-infected animals. Moreover, diffuse macroscopic GFP expression in the lung was detected 9 dpi in one SVV-GFP-infected animal.

Figure 10:
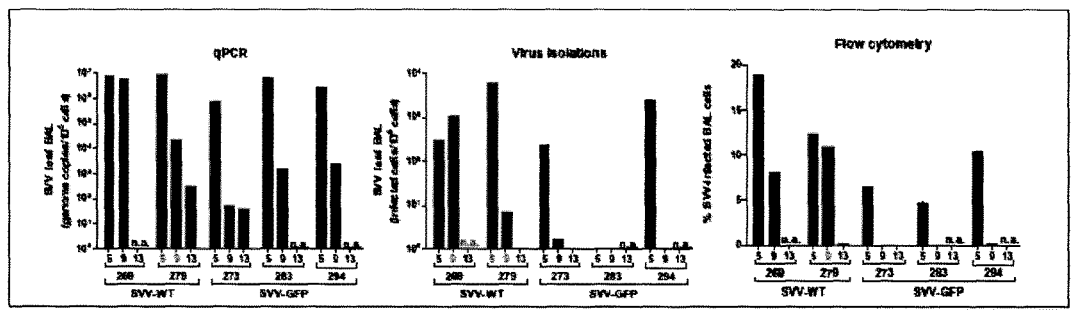
FIG. 10 contains the results of an analysis of BAL from African green moneys experimentally infected with SVV (Delta herpesvirus strain) isolated from a naturally infected monkey (E. patas) (wt SVV) and SVV-EGFP, 5 dpi. African green monkeys were inoculated with wt SVV (269 and 279) or SVV-EGFP (273,283,294) and BAL were analyzed for virus DNA by qPCR, replicating virus-infected cells by virus isolation and flow cytometry.

As shown in FIG. 10, an analysis was made of BAL from African green moneys experimentally infected with SVV (Delta herpesvirus strain) isolated from a naturally infected monkey (E. patas) (wt SVV) and SVV-EGFP, 5 dpi. African green monkeys were inoculated with wt SVV (269 and 279) or SVV-EGFP (273,283,294) and BAL were analyzed for virus DNA by qPCR, replicating virus-infected cells by virus isolation and flow cytometry.

It was found that virus replication in BAL peaked 5 dpi as detected by qPCR, virus isolation and flow cytometry (FIG. 10) and virus infected both non-lymphoid lung cells and lymphocytes showing a preference for T-cells, dendritic cells and alveolar macrophages. SVV induced a profound viremia, that peaked at 5-7 dpi and the viral infection involved both granulocytes and lymphocytes. SVV infected multiple lymphocyte subsets, though most SVV-infected cells were T-cells and NK-cells. Within SVV-infected T-cells, SVV showed a preference for CD8-bright and CD4+ T-cells. In SVV skin lesions, T-cells, dendritic cells and macrophages were infected while most SVV-infected skin-resident T-cells were CD8-dim effector memory (EM) T-cells. SVV-infected skin-resident T-cells were almost exclusively of the CD4+ central memory (CM) phenotype.

A similar approach may be used to analyze BAL and blood from Indian rhesus macaques inoculated with the SVV ORF 63 conditional mutant (mutant 2) to determine the dpi at which SVV-specific immunity is achieved. This will further corroborate that the analogous human conditional VZV mutant will elicit protective immunity and help select the dose of the mutant that should preferably be used to confer immunity in humans against VZV.

Example 6

Infection of Indian Rhesus Macaques RM with SVV Mutant 2 and SVVEGFP

As shown in FIG. 11, four Indian rhesus macaques which were used for experimental inoculation which were divided into two groups. The monkeys will be then inoculated intrabronchially with either SVV mutant 2 (group 1) or SVVEGFP (group 2). In each group, one of the monkeys will be treated with 3.3 mg/kg of TMP for 3 days. The monkeys will then be inoculated intrabronchially with either SVV mutant 2 (group 1) or SVVEGFP (group 2). The monkeys will be sacrificed on 14 dpi and tissues were collected for analysis.

One monkey for each group was treated with 3.3 mg/kg of TMP for 3 days. The second one each group was untreated. The monkeys were then inoculated intrabronchially with $6 \times 10^4$ pfu of either SVV mutant 2 (group 1) or SVVEGFP (group 2). No varicella rash was seen in any of the monkeys. The monkeys were euthanized on 14 dpi and ganglia were collected for analysis.

Example 7

Reactivation of wt SVV by Immunosuppression of Latently Infected Indian RM

Five Indian rhesus macaques were inoculated intrabronchially with wild-type SVV (HB62, H183 and HA95) or SVV-EGFP (HC44 and HF39) (Mahalingam et al., 1998). All 5 monkeys became viremic and 4 of the 5 monkeys developed varicella. The extent of rash was milder in monkeys infected with SVV-GFP. SVV and GFP-specific DNA sequences were detected in the skin rash by real-time PCR. Five months later, 2 of the monkeys inoculated with wild-type SVV (HB62 and H183) and the two monkeys inoculated with SVV-GFP (HF39 and HC44) were exposed to irradiation (200 cGy) and treated with tacrolimus (500 µg/kg/day) and prednisone (5 mg/day). In these experiments one of the monkeys inoculated with the wild-type SVV (HA95) was not immunosuppressed, but subjected to the same stress of travel and isolation. All five monkeys, including the non-immunosuppressed monkey, developed zoster rash 5-12 weeks after immunosuppression.

SVV glycoproteins gH and L were detected by immunohistochemistry in skin with zoster rash and in lung of the immunosuppressed monkeys. SVV ORF 61 transcript was detected in ganglia from the monkeys inoculated with wild-type SVV.

Because the immunosuppression protocol was observed to successfully reactivate latent SVV in different species of monkeys including Indian rhesus macaques, Cynomolgus Macaques (Mahalingam et al., 2007) and African green monkeys (Mahalingam et al., 2010), the same protocols may be used to study reactivation in Indian rhesus macaques latently infected with the SVV ORF 63 conditional mutant with and without treatment with TMP.

Example 8

Determination of Days Post Infection at which Virus-specific Immunity was Attained As described supra, the inventors constructed a SVV ORF 63/70 conditional mutant (mutant 2) in which ORF 63 is replaced with RFP and ORF 70 is fused to a destabilization domain. In the presence of the commonly used antibiotic TMP, ORF 70 protein is stable and promotes active SVV replication. Primary infection in Indian rhesus macaques will be used to determine the dpi at which virus-specific immunity is reached. In addition, we will use immunosuppressive regimens that produce zoster in monkeys to determine the role of SVV ORF 63 in varicella reactivation. Because VZV is an exclusively human virus and the current live attenuated vaccine can reactivate to produce zoster, particularly in immunosuppressed individuals, successful results of these experiments will further corroborate the efficacy of a live human varicella vaccine in which ORF 63 expression is conditionally blocked (and the virus is therefore unlikely to reactivate, while still inducing a strong humoral and cell-mediated immune response).

Example 9

Determine the Time Point Post-infection for Mutant 2 when the Protective Adaptive SVV-specific Immunity is Established Most humans develop a strong humoral and cell-mediated immune response after varicella. Reported experiments have shown that experimental inoculation of wild type SVV into rhesus macaques produce a strong humoral and cell-mediated immune response to SVV (Messaoudi et al., 2009; Ouwendijk et al., 2012). SVV DNA is present in PBMC and BAL two weeks post inoculation (p.i.). Robust B- and T-cell responses are seen in PBMC and BAL 7-14 days p.i.

For a varicella vaccine to be effective, development of a good humoral and cell-mediated immune response during primary infection is essential. Thus, active replication of SVV mutant 2 will be promoted by treating monkeys with TMP immediately before and soon after inoculation and BAL and blood samples will be examined for viremia. Afterward the treated monkeys will be challenged with wt SVV 30 days later to determine the time-point at which SVV-specific immunity is established. The methods and experiments to be used are described below.

i. Monkey Infection:

SVV mutant 2 is propagated in rhesus fibroblasts and a virus stock is prepared as described (Mahalingam et al., 1992). Twelve SVV-seronegative Indian rhesus macaques (2-4 yr old) are given trimethoprim (TMP) tablets 20 mg/day and 4 other monkeys (control) will not be given TMP. TMP tablets are crushed, dissolved into syrup, and put into fruit and hand fed. Three days later, all 16 monkeys are anesthetized and intrabronchially inoculated with $1 \times 10^5$ plaque forming units (pfu), of SVV mutant 2 as described (Mahalingam et al., 1991). The 12 monkeys treated with TMP are divided into 3 groups of 4 monkeys each. The 3 groups are treated with TMP for 3, 6 and 12 dpi, respectively. Blood samples are collected at 3, 6, 10 and 12 dpi to measure viremia. At the time of rash, punch biopsies of skin tissue with and without rash are collected and fixed in paraformaldehyde and paraffin-embedded.

SVV challenge and collection of tissues. Thirty days after SVV inoculation, all 16 monkeys are anesthetized and challenged with $1 \times 10^5$ pfu of wt SVV. BAL and blood samples are collected at 3, 6, 10, 12 and 14 days post challenge (dpc). At 14 dpc, at the expected peak of the adaptive immune response, 2 monkeys from each of the 4 groups are euthanized by sedation with ketamine (20 mg/kg body weight) followed by exsanguination and the remainder of the monkeys are euthanized at 60 dpc (latency). Blood, skin, lungs, liver, spleen, adrenal glands, ganglia, tonsils and draining lymph nodes are collected from these monkeys and included in the analysis described below. Tissue samples are collected in three different ways depending on the subsequent assays to be performed. Thus, part of the tissue sample for ex vivo flow cytometric analyses are placed in PBS, while another portion of the tissue sampled for immunohistochemistry are placed in 4% PFA and paraffin-embedded for further analysis.

ii. Analysis of SVV-specific T- and B-cell Response and Viremia.

Lymphocytes are isolated from heparinized blood samples by density gradient-centrifugation. PBMCs are subjected to flow cytometry analysis to identify SVV-infected PBMC cell types as described (Ouwendijk et al., 2012; 2013). In parallel, plasma samples are analyzed by ELISA (Ouwendijk et al., 2012) to determine SVV-specific IgM and IgG antibody levels.

iii. Analysis of Tissues for SVV DNA, RNA and Protein.

DNA are isolated from one-fifth of the PBMC cell suspension with the MagnaPure DNA Tissue Kit II (Roche) using the MagnaPure LC Isolation station according to the manufacturer's instructions (Roche). Snap-frozen tissues are divided into three unequal portions. Total DNA is extracted from the smaller portion using a DNeasy Tissue kit (Qiagen, Ventura, Calif.) according to the manufacturer's instructions. SVV DNA-positive ganglia are identified by PCR. Total RNA is extracted from the largest portion of ganglia (positive for SVV DNA) and treated with DNase as described (White et al., 2002). To determine the SVV DNA copy number in PBMCs as well as tissues, quantitative PCR is performed on an ABI Prism 7700 using the TaqMan Universal Master Mix (both from Applied Biosystems, Foster City, Calif.). Sequences and target genes of the primers/probe pairs and reaction conditions are based on previously published information (Messaoudi et al., 2009). PCR analysis will include primers that overlap the degradation domain and SVVORF 70 sequences.

iv. Flow Cytometric Analyses of Resident Cells and Infiltrating Lymphocytes in Dissected Tissues.

Tissue specimens collected in PBS are homogenized in PBS containing 1% BSA (iP1B medium) and subsequently treated with Liberase blendzyme 3 (0.2 U/ml) at 37° C. for 1 hr. Dispersed cell suspensions are filtered through a 100-μm pore-size mesh, and the flow-through are collected and resuspended in P1B medium. We will use both commercially available fluorochrome-conjugated mAbs cross-reactive with macaque lymphocytes as described (Swart et al., 2007). About 106 PBMCs are used for staining, and more than $5 \times 10^5$ viable lymphocyte events are obtained on a FACSCalibur (BD Biosciences) to enable detection of low-frequency EGFP$^+$ subpopulations. Initially, we will focus on general lymphocyte populations such as monocytes, T, B and NK cells. Based on previous studies, we expect EGFP$^+$ lymphocytes to be mainly CD4$^+$ T cells. EGFP$^+$ T cells identified as CD4$^+$ or CD8$^+$, are analyzed in detail with respect to their activation, i.e. HLA-DR+ and differentiation status, i.e. naïve (CD45RA+CD28+) versus memory T cells (CD45RA$^-$CD28$^-$), and for EGFP$^+$ memory T cells, effector (CD62L−) versus central memory (CD62L$^+$) T cells.

v. Immunohistochemical Analyses.

Paraffin-embedded tissues are sectioned (6-10 μm) with a microtome for immunohistochemical analysis as described (Messaoudi et al., 2009). Additional markers of interest are CD45 (leukocytes), CD3 and CD8 (T cells), CD21 and CD20 (B cells), CD68 (macrophages), CD11c (dendritic cells) and HLA class II (activation marker). Antibodies to EGFP and SVV ORF 63 are used to detect SVV-infected cells.

Example 10

Determination of the Role of SVV ORF 63 Expression in Reactivation from Latency in Monkeys VZV infects only humans. Although human tissues obtained at autopsy have been used to study varicella latency, it is impossible to study reactivation. We have demonstrated that latent SVV can be reactivated in African green monkeys, Cynomologous and Indian RM (Mahalingam et al., 2007; 2010 and Preliminary Results). SVV ORF 63/70 expression is required for efficient virus replication in culture. Inoculation of mutant 2 produces chickenpox in TMP-treated Indian RM but not in untreated monkeys. Since, SVV ORF 63/70 is required for SVV replication; we will immunosuppress monkeys latently infected with mutant 2, with and without TMP-treatment, to confirm that the conditional SVV mutant can be used as a vaccine to prevent reactivation. The experimental methods are described below.

i. Establishment of Latent SVV Infection in Monkeys and Harvesting of Latently Infected Tissues.

Eight SVV-seronegative Indian RM (2-4 years old) are given trimethoprim (TMP) tablets 20 mg/day. Three days later, all 8 monkeys are anesthetized and intrabronchially inoculated with $1 \times 10^5$ plaque forming units (pfu), of SVV mutant 2 as described (Mahalingam et al., 1991). Blood samples are collected at 3, 6, 10 and 12 dpi to measure viremia. At the time of rash, punch biopsies of skin tissue with and without rash are collected and fixed in paraformaldehyde and paraffin-embedded.

ii. Treatment of Monkeys with Immunosuppressive Regimens.

Sixty days after inoculation (after the establishment of latency), the 8 monkeys are divided into 2 groups of 4 monkeys each. One group of monkeys (group 1) are given TMP tablets (20 mg/day) the other group will not be given TMP. Three days later, all 8 latently infected monkeys are immunosuppressed as described (Mahalingam et al., 2007; 2010). Briefly, monkeys are given a one-time dose of 200 cGy of X-irradiation along with tacrolimus at 100 mg/kg/day and prednisolone (oral) at 2 mg/kg/day for 1 month. The monkeys are transported to the Radiation Oncology Facility at the Tulane Medical Center, New Orleans, La. Dr. Ellen Zakris, Chief of Tulane Radiation Oncology, Tulane Cancer Center, and Director of Radiation Oncology Programs, will oversee the X-irradiation treatment.

iii. Harvest of Ganglionic and Non-ganglionic Tissues.

All monkeys are observed daily for zoster rash. Under anesthesia, monkey with zoster rash are punch-biopsied in the area of rash and the sample are fixed in 4% PFA and paraffin-embedded. All monkeys are euthanized at the time of rash. Lung and liver tissues are harvested and divided into two portions. One portion is snap-frozen for extraction of DNA and RNA. The other portion are fixed in 4% PFA and paraffin-embedded. Ganglia on the two sides of the neuraxis are kept separately. Ganglia from each dermatome are pooled. Dermatomes associated with zoster rash are identified and the corresponding ganglia are processed separately. Pooled ganglia from specific regions from one side of the neuraxis are snap-frozen in liquid nitrogen, while pooled ganglia from the same dermatomes of the other side are fixed in 4% PFA and paraffin-embedded. We do not expect rash to develop in monkeys not treated with TMP. They are euthanized one week after the last set of monkeys develop rash.

iv. DNA and RNA Isolation, PCR and RT-PCR.

Extraction of DNA, RNA from tissues including blood and PCR and RT-PCR are performed as described supra.

v. Immunohistochemistry.

Immunohistochemical analysis of fixed skin, lungs and ganglia are performed as described supra.

Relevance of Results of these Experiments:

The results of the afore-described experiments should confirm that the latent form of the conditional mutant (mutant 2) of the simian varicella virus reactivates only in the presence of TMP but not in its absence. This will corroborate the efficacy of the analogous human varicella virus conditional mutants for use in the development of novel varicella vaccines. To further confirm safety and efficacy we will further confirm there is no low level subclinical reactivation of mutant 2 in the absence of zoster rash. To do so we will analyze non-ganglionic tissues including lung and liver for virus DNA. The presence of DNA sequences specific for mutant 2 will indicate subclinical reactivation.

Example 11

Construction of Mutated SVV and Demonstration that SVV Replication is Conditionally Blocked and the Blockade is Reversible by Addition of TMP As shown in FIG. 12, the present inventors constructed mutant SVV wherein the genomes of wild type and mutant SVV in which EGFP and the bacmid vector sequences have been removed. Also, in the mutant SVV, ORF63 was replaced with RFP (red fluorescent protein) As shown in FIG. 13, there was a pronounced reduction in number of mutant SVV plaques at different tested amounts of the TMP antibiotics (100 nM, 100 nM and 10 nM), In fact, as can be seen in Panel C of he figure at 10 nM a single plaque was barely visible.

In addition, experiments were conducted demonstrating that the impaired replication of SVV replication is reversible. As shown in FIG. 14 the virus does not substantially replicate in infected cells after TMP is removed (after initial induction of replication by the addition of TMP antibiotic). By contrast, replication of SVV is restored when TMP is added back to the SVV culture. Therefore, the results in the FIG. 14 demonstrate that the effect of TMP on mutant SVV replication is reversible.

Example 12

Effect of TMP on SVV IE63 Expression

Figure 15:
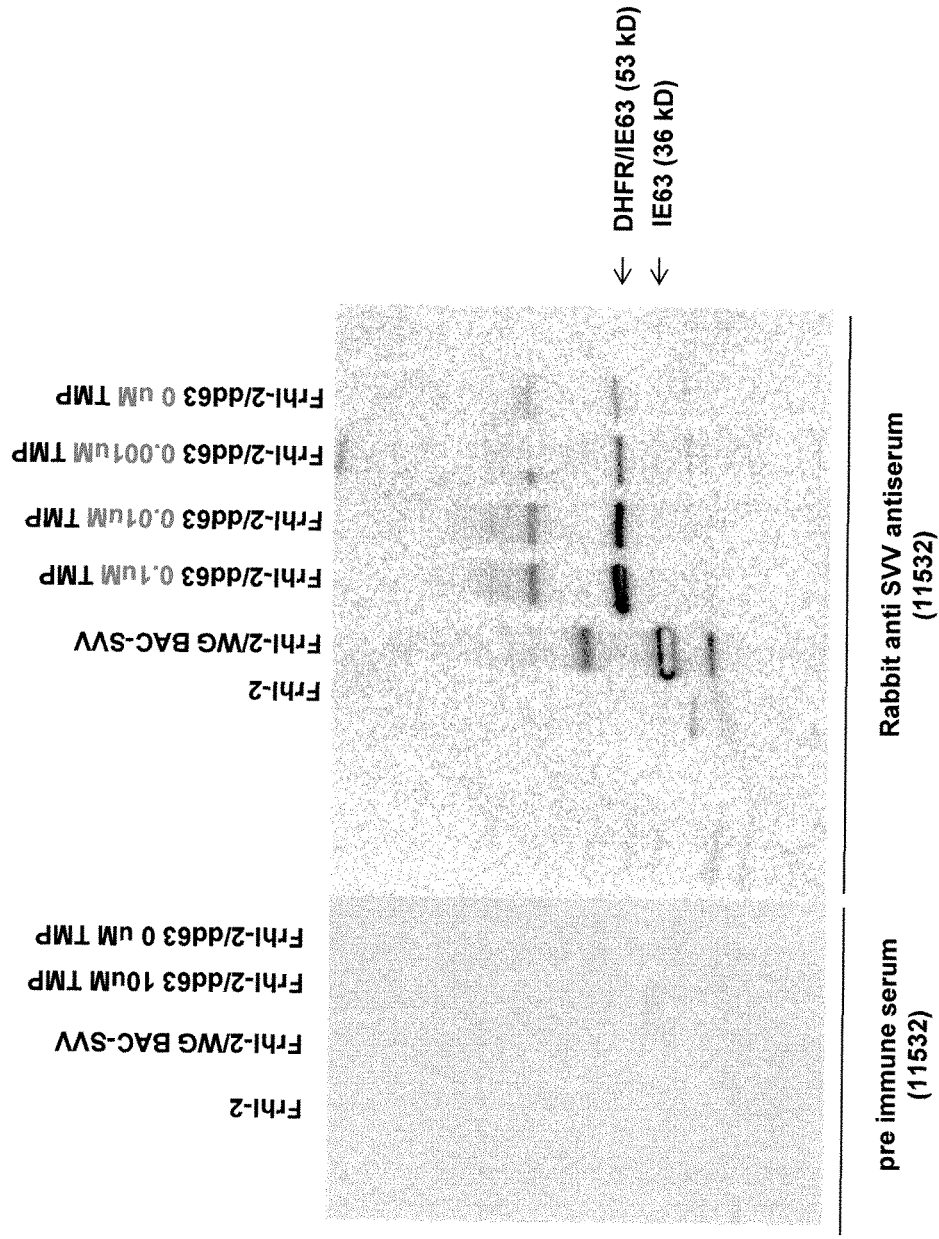
FIG. 15 contains the results of an experiment showing lysates of rhesus fibroblasts (Frhl-2) infected with the SVV mutant grown at different concentrations of TMP was analyzed on a Western blot using rabbit pre-immune serum or rabbit polyclonal against SVV ORF 63 peptides. Panel on the right shows a dramatic reduction in the ORF63-DHFR fusion protein with decreasing TMP concentration. Pre-immune serum did not show any reactivity.

The inventors also conducted experiments to assess the effect of different TMP concentrations on the expression of the SVV IE63. In these experiments lysates of rhesus fibroblasts (Frh1-2) infected with the SVV mutant were grown at different concentrations of TMP. Afterward the lysates were analyzed on a Western blot using rabbit pre-immune serum or rabbit polyclonal antibody against SVV ORF 63 peptides. It can be seen from the panel on the right of FIG. 15 that three is a dramatic reduction in the amount of ORF63-DHFR fusion protein as the concentration of the TMP in the lysate is decreased. Moreover, the experiments revealed that the pre-immune serum did not show any reactivity. These results further corroborate that the incorporation of one or more destabilization domains onto essential herpesvirus genes (genes required for virus replication) is an effective means of providing for controlled replication of the virus when the induction (TMP) conditions are present and substantially no replication when the induction conditions are absent.

Example 13

Effect of DHFR Destabilization Domain on Growth of SVV

Figure 16:
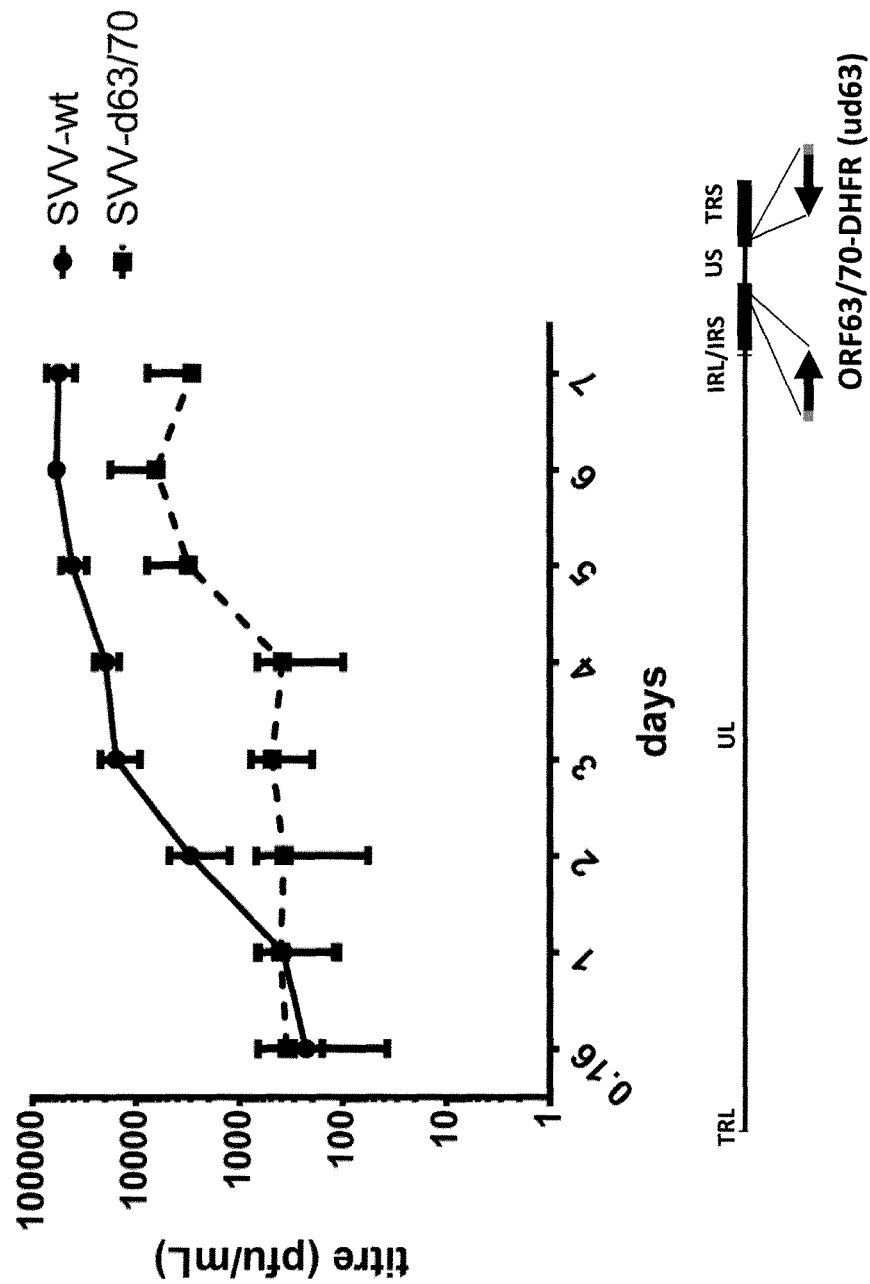
FIG. 16 shows that a mutant SVV (containing DHFR fused at the N-terminal end of ORF 63 and 70) grows slower than the wild type SVV in rhesus fibroblasts.

Experiments were further conducted comparing the growth of wild type SVV and mutated SVV strain according to the invention in rhesus fibroblasts. As shown in the growth curve experiments in FIG. 16 the mutant virus (SVV containing DHFR fused at the N-terminal end of ORFs 63 and 70) grows slower than the wild type SVV in rhesus fibroblasts.

Example 14

In Vivo Effect of Mutant SVV Administered by Intrabronchial Inoculation in Rhesus Macaques In vivo experiments were further conducted assessing the effects of mutant SVV in rhesus macaques. In these experiments SVV-seronegative rhesus macaques were inoculated intrabronchially with the mutant SVV. This inoculation was effected both in the presence or absence of 20 mg/kg of TMP. After inoculation the animals were euthanized and their tissues analyzed by PCR for the presence of SVV DNA. As shown schematically in FIG. 17, these animals did not exhibit rash or viremia.

Example 15

Construction of Mutant SVV Wherein DHFR Destabilization Domain is Fused at the C-Terminus of ORF63/70

The present inventors observed that when the DHFR destabilization domain was fused at the 5" end of the ORF63 or ORF70 that the virus grew slower. Therefore the inventors prepared another mutant in which the DHFR sequences were fused at the 3'-end.

Figure 20:
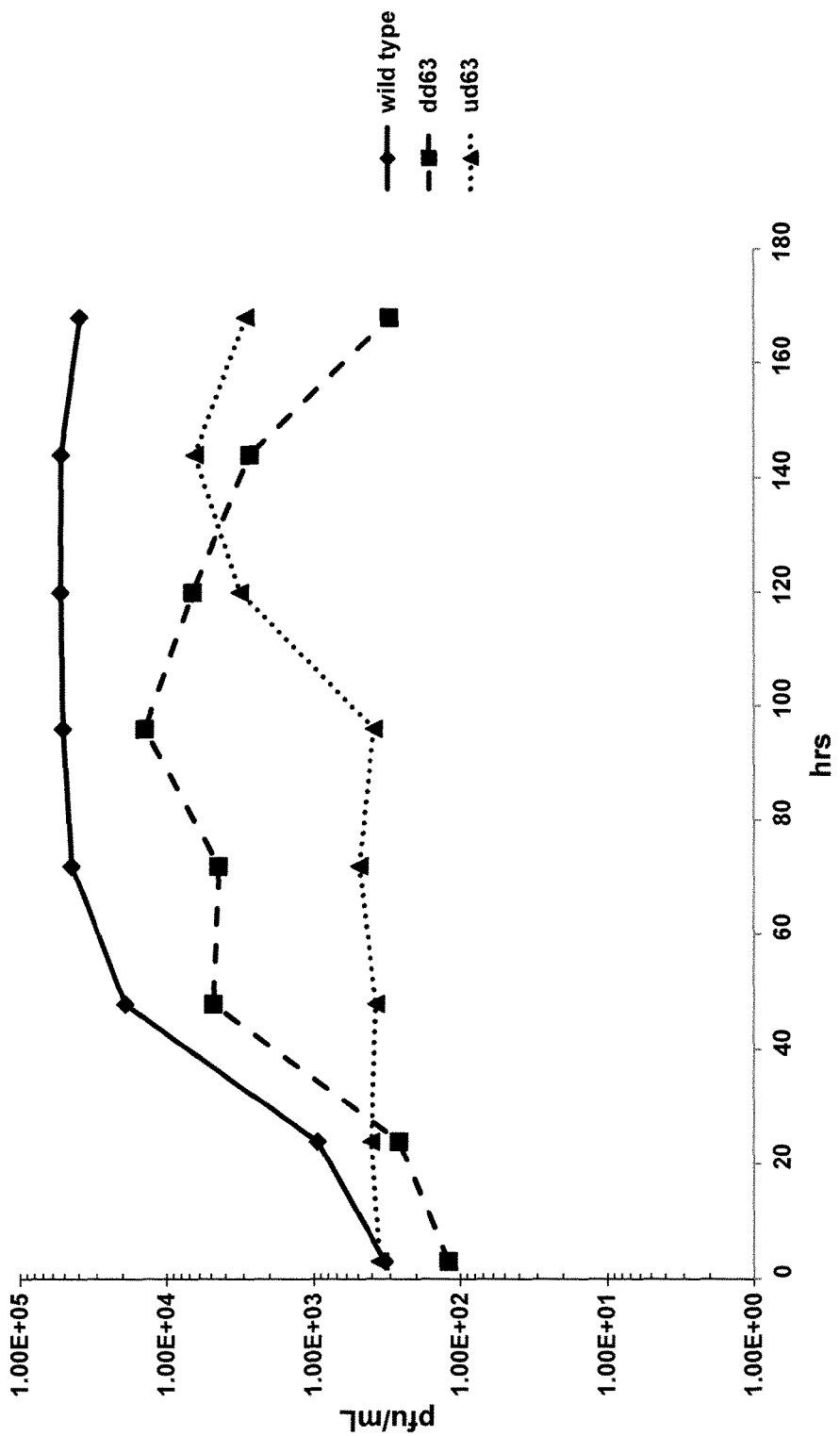

As shown by the comparison of the growth curves (FIG. 20), of this mutant, the wild-type SVV and the prior SVV mutant (ud63) (wherein the DHFR was fused at the N-terminal end of ORF63/70) demonstrated that the mutant SVV (dd63) wherein DHFR is fused at the C-terminal end of the ORF63/70 grew better than the older SVV mutant (ud63-DHFR fused at the N-terminal end).

Example 16

Construction of Mutant HSV-1 Wherein DHFR Destabilization Domain is Fused at the N-Terminus of DNA Polymerase Gene In order to further validate that the claimed virus mutation approach may be used to design other modified herpesviruses that replicate only under inducible conditions and which may be used in the preparation of prophylactic vaccines the present inventors constructed a similarly modified HSV-1 virus. The structure of this modified HSV-1 virus is contained in FIG. 21.

Figure 21:
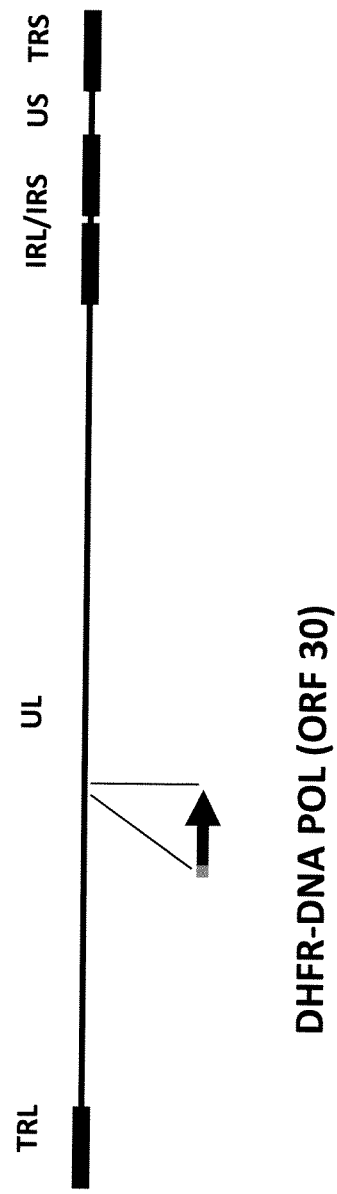

FIG. 21 shows the genome of a constructed mutant HSV-1 in which DHFR is fused to the N-terminal end of a gene essential for HSV-1 viral replication, i.e., the DNA polymerase gene. In addition experiments were conducted to assess whether the replication of this mutant is TMP dependent. As shown by the experiments in FIG. 22 there were a reduced number of plaques with the HSV-1 mutant in the absence of TMP. By contrast, as expected the same cells infected with wild type HSV were blown away by infection (data not shown).

Based on the similar genome of HSV-1 and HSV-2 it is anticipated that similar changes in HSV2 should result in a conditionally replication deficient HSV-2 strain that should be useful in vaccines for generating long-lived protective immunity to HSV-2, and moreover vaccines containing these modified strains should prevent the reoccurrence of HSV-1 or HSV-2 infection and the adverse effects thereof such as oral or genital lesions.

REFERENCES CITED IN PATENT APPLICATION

1. Arvin, A. M. and A. A. Gershon. 1996. Live attenuated varicella vaccine. Annu. Rev. Microbiol. 50:59-100.
2. Breuer, J. 2001. Vaccination to prevent varicella and shingles. Journal of Clinical Pathology 54:743-747.
3. Chen, J. J., A. A. Gershon, Z. S. Li, O. Lungu, and M. D. Gershon. 2003. Latent and lytic infection of isolated guinea pig enteric ganglia by varicella zoster virus. J. Med. Virol. 70 Suppl 1:S71-S78.
4. Debrus, S., C. Sadzot-Delvaux, A. F. Nikkels, J. Piette, and B. Rentier. 1995. Varicella-zoster virus gene 63 encodes an immediate-early protein that is abundantly expressed during latency. J. Virol. 69:3240-3245.
5. Dendouga, N., M. Fochesato, L. Lockman, S. Mossman, and S. L. Giannini. 2012. Cell-mediated immune responses to a varicella-zoster virus glycoprotein E vaccine using both a TLR agonist and QS21 in mice. Vaccine 30:3126-3135.
6. Goldman, G. S. and P. G. King. 2012. Review of the United States universal varicella vaccination program: Herpes zoster incidence rates, cost-effectiveness, and vaccine efficacy based primarily on the Antelope Valley Varicella Active Surveillance Project data. Vaccine.
7. Iwamoto, Tomas Bjorklund, Cecilia Lundberg, Deniz Kirik, and Thomas J. Wandles et al., 2010, A General Chemical Method to Regulate Protein Stability in the Mammalian Central Nervous System; Chem. & Biol. 17:981-988.
8. Kennedy, P. G., E. Grinfeld, S. Bontems, and C. Sadzot-Delvaux. 2001. Varicella-zoster virus gene expression in latently infected rat dorsal root ganglia. Virology 289:218-223.
9. Krause, P. R. and D. M. Klinman. 2000. Varicella vaccination: evidence for frequent reactivation of the vaccine strain in healthy children. Nat. Med. 6:451-454.
10. Lowry, P. W., C. Sabella, C. M. Koropchak, B. N. Watson, H. M. Thackray, G. M. Abbruzzi, and A. M. Arvin. 1993. Investigation of the pathogenesis of varicella-zoster virus infection in guinea pigs by using polymerase chain reaction. J. Infect. Dis. 167:78-83.
11. Mahalingam, R., M. Wellish, W. Wolf, A. N. Dueland, R. Cohrs, A. Vafai, and D. Gilden. 1990. Latent varicella-zoster viral DNA in human trigeminal and thoracic ganglia. N. Engl. J. Med. 323:627-631.
12. Oxman, M. N., M. J. Levin, G. R. Johnson, K. E. Schmader, S. E. Straus, L. D. Gelb, R. D. Arbeit, M. S. Simberkoff, A. A. Gershon, L. E. Davis, A. Weinberg, K. D. Boardman, H. M. Williams, J. H. Y. Zhang, P. N. Peduzzi, C. E. Beisel, V. A. Morrison, J. C. Guatelli, P. A. Brooks, C. A. Kauffman, C. T. Pachucki, K. M. Neuzil, R. F. Betts, P. F. Wright, M. R. Griffin, P. Brunell, N. E. Soto, A. R. Marques, S. K. Keay, R. P. Goodman, D. J. Cotton, J. W. Gnann, J. Loutit, M. Holodniy, W. A. Keitel, G. E. Crawford, S. S. Yeh, Z. Lobo, J. F. Toney, R. N. Greenberg, P. M. Keller, R. Harbecke, A. R. Hayward, M. R. Irwin, T. C. Kyriakides, C. Y. Chan, I. S. F. Chan, W. W. B. Wang, P. W. Annunziato, and J. L. Silber. 2005. A vaccine to prevent herpes zoster and postherpetic neuralgia in older adults. New England Journal of Medicine 352:2271-2284.
13. Ouwendijk, W. J. D., Mahalingam, R., de Swart, R. L., Haagmans, B. L., vanAmerongen, G., Getu S., Gilden, D., Osterhaus, A. D. M. E., and Verjans, G. M. G. M. T-Cell Tropism of Simian Varicella Virus During Primary Infection. 2013. PLoS pathogens 9 (5) e1003368.
14. Quan, D., R. J. Cohrs, R. Mahalingam, and D. H. Gilden. 2007. Prevention of shingles: safety and efficacy of live zoster vaccine. Ther. Clin. Risk Manag. 3:633-639.
15. Sadzot-Delvaux, C., M. P. Merville-Louis, P. Delree, P. Marc, J. Piette, G. Moonen, and B. Rentier. 1990. An in vivo model of varicella-zoster virus latent infection of dorsal root ganglia. J. Neurosci. Res. 26:83-89.
16. Tenser, R. B. and R. W. Hyman. 1987. Latent herpesvirus infections of neurons in guinea pigs and humans. Yale J. Biol. Med. 60:159-167.
17. Tischer, B. K., E. J. von, B. Kaufer, and N. Osterrieder. 2006. Two-step red-mediated recombination for versatile high-efficiency marker-less DNA manipulation in *Escherichia coli*. Biotechniques 40:191-197.
18. Vafai, A. 1995. Boosting immune response with a candidate varicella-zoster virus glycoprotein subunit vaccine. Vaccine 13:1336-1338.
19. White, T. M., R. Mahalingam, V. Traina-Dorge, and D. H. Gilden. 2002. Simian varicella virus DNA is present and transcribed months after experimental infection of adult African green monkeys. J. Neurovirol. 8:191-203.
20. Wroblewska, Z., T. Valyi-Nagy, J. Otte, A. Dillner, A. Jackson, D. P. Sole, and N. W. Fraser. 1993. A mouse model for varicella-zoster virus latency. Microb. Pathog. 15:141-151.

Each reference cited herein is hereby incorporated by reference in its entirety.

The invention is further described by the following claims.

What is claimed is:

1. A vaccine composition comprising a mutated, recombinant Herpesviridae strain which corresponds to a wild-type Herpesviridae strain having a first copy and a second copy of at least one gene that is essential for viral replication, wherein the first copy and the second copy of the at least one gene are independently fused to at least one destabilization domain, wherein the strain is conditionally replication deficient and substantially replicates only when the strain is contacted with a compound, and wherein each occurrence of the destabilization domain independently comprises an *Escherichia coli* dihydrofolate hydroxylase (DHFR) destabilization domain, and wherein the compound comprises trimethoprim (TMP).

2. The vaccine composition of claim 1, wherein at least one applies:

(i) the destabilization domain is fused to the carboxy-terminus of the first copy or second copy of the at least one gene that is essential for viral replication;

(ii) the destabilization domain is fused to the amino-terminus of the first copy or second copy of the at least one gene that is essential for viral replication;
(iii) the mutated, recombinant Herpesviridae strain is selected from the group consisting of Varicella-zoster virus and Simian varicella virus;
(iv) the mutated, recombinant Herpesviridae virus is a Varicella-zoster virus or Simian varicella virus strain, wherein at least one gene that is essential for viral replication is selected from the group consisting of Gene or ORF 63/70, and Gene or ORF 62/71;
(v) the mutated, recombinant Herpesviridae viral strain is a human varicella zoster virus.

3. The vaccine composition of claim 2, wherein the vaccine composition comprises a combination or multivalent vaccine that affords immunity against at least one Herpesviridae strain and another virus selected from the group consisting of another Herpesviridae strain, mumps, rubella, tetanus, diphtheria, human papilloma, measles virus, and any combinations thereof.

4. An isolated cell that has been transfected with the vaccine composition of claim 2.

5. A method for eliciting protective immunity against at least one Herpesviridae strain, which comprises the following steps:
(i) administering to a host that is susceptible to infection by at least one Herpesviridae strain a vaccine that comprises an effective amount of a therapeutically effective amount of the vaccine composition of claim 1; and
(ii) before, concomitant or after the administration of said vaccine, further administering to said host TMP, resulting in the conditional expression of the first and second copies of the at least one gene essential for viral replication, wherein the first and second copies are independently fused to the destabilization domain, and allowing the virus to replicate for a sufficient time to allow the susceptible host to develop protective immunity against the at least one Herpesviridae strain.

6. A method for boosting protective immunity in an individual who has been previously vaccinated against at least one Herpesviridae strain by the immunization of said individual with a therapeutically effective amount of the vaccine composition of claim 1, wherein the method comprises administering to said individual TMP, resulting in the conditional expression of the first and second copies of the at least one gene essential for viral replication, wherein the first and second copies are independently fused to the destabilization domain, and allowing the at least one Herpesviridae virus to replicate for a sufficient time to allow the individual to boost their protective immunity against the at least one Herpesviridae strain.

7. A vaccine composition comprising a mutated, recombinant human or primate varicella virus, wherein the wild-type varicella virus without any mutation is prone to establishing latency in ganglia and reactivating after administration resulting in the onset of shingles or zoster,
wherein the genomic DNA of the varicella virus is modified to produce a conditional replication deficient varicella virus vaccine strain that replicates only when contacted with a compound,
wherein a first copy and a second copy of an essential gene of the conditional replication deficient varicella virus vaccine strain required for viral replication is independently fused to at least one destabilization domain gene,
wherein each occurrence of the destabilization domain independently comprises an *Escherichia coli* dihydrofolate hydroxylase (DHFR) destabilization domain, and
wherein the compound comprises trimethoprim (TMP).

8. The vaccine composition of claim 7, wherein
(i) the destabilization domain is fused to the 5' or 3' end of the first copy or second copy of the essential gene; and
(ii) the essential gene is selected from the group consisting of gene 63, gene 70, gene 62, and gene 71.

9. The vaccine composition of claim 7, wherein at least one applies:
(i) the mutated, recombinant virus comprises a mutated varicella zoster virus (VZV) vaccine strain;
(ii) the mutated, recombinant virus comprises a mutated simian varicella virus (SVV) vaccine strain;
(iii) the mutated, recombinant virus comprises a mutated OKA VZV strain;
(iv) the destabilization domain is fused to the amino terminus of gene 63 or gene 70;
(v) the destabilization domain is fused to the carboxy terminus of gene 63 or gene 70;
(vi) the destabilization domain is fused to the amino terminus of gene 62 or 71;
(vii) the destabilization domain is fused to the carboxy terminus of gene 62 or 71;
(viii) the mutated, recombinant virus further comprises a gene that encodes a detectable polypeptide, which is optionally green or red fluorescent polypeptide (GFP or RFP);
(ix) the mutated, recombinant virus does not reactivate after administration to a susceptible host; or
(x) the mutated, recombinant virus is a VZV and does not reactivate for the lifetime of an individual vaccinated with the mutated, recombinant virus.

10. The vaccine composition of claim 9, which further comprises compositions that confer protection against other viruses selected from the group consisting of attenuated mumps, measles, and diphtheria virus.

11. A method of immunizing a susceptible mammal against Varicella virus wherein the administered Varicella virus is not susceptible to reactivation after immunization, wherein the method comprises administering a vaccine comprising a therapeutically effective amount of the vaccine composition of claim 1 comprising a mutated, recombinant Herpesviridae strain, wherein the strain is a Varicella virus.

12. A method of preparing the vaccine composition of claim 1, wherein the method comprises mutating the Herpesviridae strain virus, wherein the strain is VZV or SVV, wherein the method is selected from the group consisting of:
(i) fusing a nucleic acid encoding a destabilization domain to a first copy of an essential gene, which comprises gene 63 or gene 62 of a VZV or SVV, and fusing a nucleic acid encoding a destabilization domain to a second copy of the essential gene, which comprises gene 70 of VZV or gene 71 of SVV, and wherein each occurrence of the destabilization domain independently comprises an *Escherichia coli* dihydrofolate hydroxylase (DHFR) destabilization domain thereby producing a conditionally, replication deficient VZV or SVV strain.

13. The method of claim 12, wherein the recombinant VZV replicates only in the presence of the antibiotic trimethoprim (TMP).

14. The vaccine composition of claim 2, which comprises a mutated, recombinant human or primate varicella virus wherein gene 63 is fused to a destabilization domain, and gene 70 is fused to a destabilization domain.

15. The vaccine composition of claim 2, which comprises a mutated, recombinant human or primate varicella virus, wherein gene 62 is fused to a destabilization domain and gene 71 is fused to a destabilization domain.

16. An immunogenic composition comprising a mutated, recombinant Herpesviridae strain which corresponds to a wild-type Herpesviridae strain having a first copy and a second copy of at least one gene that is essential for viral replication,
   wherein the first copy and the second copy of the at least one gene are independently fused to at least one destabilization domain,
   wherein the strain is conditionally replication deficient and substantially replicates only when the strain is contacted with a compound, and
   wherein each occurrence of the destabilization domain independently comprises an *Escherichia coli* dihydrofolate hydroxylase (DHFR) destabilization domain,
   wherein the compound comprises trimethoprim (TMP), and
   the mutated, recombinant Herpesviridae strain is selected from the group consisting of HSV-1 and HSV-2.

* * * * *